US007056683B2

(12) United States Patent
Ting

(10) Patent No.: US 7,056,683 B2
(45) Date of Patent: Jun. 6, 2006

(54) GENETICALLY ENCODED FLUORESCENT REPORTERS OF KINASE, METHYLTRANSFERASE, AND ACETYL-TRANSFERASE ACTIVITIES

(75) Inventor: Alice Y. Ting, Allston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 10/634,740

(22) Filed: Aug. 5, 2003

(65) Prior Publication Data
US 2004/0265906 A1    Dec. 30, 2004

Related U.S. Application Data

(60) Provisional application No. 60/425,578, filed on Nov. 12, 2002.

(51) Int. Cl.
G01N 33/53 (2006.01)

(52) U.S. Cl. ............... 435/7.1; 435/194; 530/358

(58) Field of Classification Search ............... 435/6, 435/194, 7.1, 69.1, 69.7, 320.1; 530/350, 530/358
See application file for complete search history.

(56) References Cited

U.S. PATENT DOCUMENTS

| 5,503,977 | A | 4/1996 | Johnsson et al. |
| 5,585,245 | A | 12/1996 | Johnsson et al. |
| 5,625,048 | A | 4/1997 | Tsien et al. |
| 6,124,128 | A | 9/2000 | Tsien et al. |
| 6,465,199 | B1 * | 10/2002 | Craig et al. ............ 435/7.4 |
| 2002/0019002 | A1 | 2/2002 | Griffiths |
| 2002/0090643 | A1 | 7/2002 | Craig et al. |
| 2002/0164674 | A1 | 11/2002 | Tsien et al. |
| 2002/0165364 | A1 | 11/2002 | Tsien et al. |
| 2003/0186229 | A1 * | 10/2003 | Tsien et al. ............ 435/6 |

FOREIGN PATENT DOCUMENTS

| WO | WO 96/23810 | 8/1996 |
| WO | WO 01/33199 A2 | 5/2001 |
| WO | WO 02/066656 A2 | 8/2002 |
| WO | WO 02/079391 A2 | 10/2002 |
| WO | WO 02/095058 A2 | 11/2002 |

OTHER PUBLICATIONS

Reichheld et al., Multilevel regulation of histone gene expression during the cell cycle in tobacco cells. Nucleic Acids Res. Jul. 1, 1998;26(13):3255-62.*
Akhtar et al., Chromodomains are protein-RNA interaction modules.Nature. Sep. 21, 2000;407(6802):405-9.*
Agalioti, T. et al, Deciphering the transcriptional histone acetylation code for a human gene. *Cell* 111: 381-392, 2002..
Ait-Si-Ali, S. et al., CBP/p300 histone acetyl-transferase activity is important for the G1/S transition. *Oncogene* 19: 2430-2437, 2000.

Belyaev, N.D. et al., Histone H4 acetylation and replication timing in Chinese hampster chromosomes. *Experimental Cell Research* 225: 277-285, 1996.
Campbell, R.E. et al., A monomeric red fluorescent protein. *Proc. Natl. Acad. Sci. USA* 99(12): 7877-7882, 2002.
Chen, H. et al., Regulation of hormone-induced histone hyperacetylation and gene activation via acetylation of acetylase. *Cell* 98: 675-686, 1999.
Cheung, P. et al., Synergistic coupling of histone H3 phosphorylation and acetylation in response to epidermal growth factor stimulation. *Molecular Cell* 5: 905-915, 2000.
Dhalluin, C. et al., Structure and ligand of a histone acetyltransferase bromodomain. *Nature* 399: 491-496, 1999.
Fischle, W. et al., Histone and chromatin cross-talk. *Current Opinion in Cell Biology* 15: 172-183, 2003.
Fu, H. et al., 14-3-3 proteins: structure, function and regulation. *Annual Review Pharmacology and Taxicology* 40: 617-647, 2000.
Goto, H. et al, Identification of a novel phosphorylation site on histone H3 coupled with mitotic chromosome condensation. *Journal of Biological Chemistry* 274: 25543-25549, 1999.
Jacobson, R.H. et al., Structure and function of a human $TAF_{11}250$ double bromodomain module. *Science* 288: 1422-1425, 2000.
Kimura, H. et al., Kinetics of core histones in living human cells: little exchange of H3 and H4 and some rapid exchange of H2B. *The Journal of Cell Bioloy* 153(7): 1341-1353, 2001.
Lachner, M. et al., The many faces of histone lysine methylation. *Current Opinion in Cell Biology* 14: 286-298, 2002.
Marmorstein, R., Protein modules that manipulate histone tails for chromatin regulation. *Nat. Rev. Mol. Cell Biol.*, 2: 422-432, 2001.
New, L. et al., Cloning and characterization of RLPK, a novel RSK-related protein kinase. *Journal of Biological Chemistry* 274 (2): 1026-1032, 1999.
Nielsen, P.R. et al., Structure of the HPI chromodomain bound to histone H3 methylated at lysine 9. *Nature* 416: 103-107, 2002.

(Continued)

*Primary Examiner*—Jon Weber
*Assistant Examiner*—Robert B. Mondesi
(74) *Attorney, Agent, or Firm*—Wolf, Greenfield & Sacks, P.C.

(57) ABSTRACT

The invention provides fusion protein reporter molecules that can be used to monitor protein modifications (e.g., histone modifications) in living cells, and methods of using the fusion reporter molecules for diagnosing protein-modification-associated disorders (e.g. histone-modification-associated disorders). The invention also provides methods of using the fusion protein reporters to identify candidate pharmaceutical agents that effect protein modification in cells and tissues, thus permitting identification of candidate pharmaceutical agents for treatment of protein-modification-associated disorders.

26 Claims, 6 Drawing Sheets

OTHER PUBLICATIONS

Perissi, V. et al., Factor-specific modulation of CREB-binding protein acetyltransferase activity. *Proc. Natl. Acad. Sci. USA* 96: 3652-3657, 1999.

Rea, S. et al., Regulation of chromatin structure by site-specific histone H3 methyltransferases. *Nature* 406: 593-599, 2000.

Shankaranarayanan, P. et al., Acetylation by histone acteyltransferase CREB-binding protein/p300 of STAT6 is required for transcriptional activation of the 15-lipoxygenase-1 gene. *The Journal of Biological Chemistry* 276(46): 42753-42760, 2001.

Tachibana, M. et al., G9a histone methyltransferase plays a dominant role in euchromatic histone H3 lysine 9 methylation and is essential for early embryogenesis. *Genes and Development* 16: 1779-1791, 2002.

Taddei, A. et al., Duplication and maintenance of heterochromatin domains. *The Journal of Cell Biology* 147: 1153-1166, 1999.

Ting, A.Y. et al., A Fluorescent probe of tyrosine phosphorylation in vivo, Grant No. IF32GM063443-01, University of California San Diego, Grant Year 2001, NIH CRISP database at http://crisp.cit.nig.gov/..

Ting, A.Y. et al., Genetically encoded fluorescent reporters of protein tyrosine kinase activities in living cells. *PNAS* 98(26): 15003-15008, 2001.

Yaffe, M.B. et al., A motif-based profile scanning appoach for genome—wide prediction of signalling pathways. *Nature Biotechnology* 19: 348-353, 2001.

Yaffe, M.B. et al., The structural basis for 14-3-3: phosphopeptide biding specificity. *Cell* 91: 961-971, 1997.

Zacharias, D.A. et al., Partitioning of lipid-modified monomeric GFPs into membrane microdomains of live cells. *Science*, 296: 913-916, 2002.

Zhang, J. et al., Creating new fluoresent probes for cell biology. *Nat. Rev. Mol. Cell. Biol.*, 3: 906-18, 2002.

Zhang, Y. et al., Transcription regulation by histone methylation: interplay between different covalent modifications of the core histone tails. *Genes and Development*, 15: 2343-2360, 2001.

Zhong, S. et al., Ultraviolet B-induced phosphorylation of histone H3 at serine 28is mediated by MSK1.*J. Biol. Chem.* 276(35), 33213-33219, 2001.

Feroli et al., Analysis of a 17-9 kb region from *Saccharomyces cerevisiae* chromosome VII reveals the presence of eight open reading frames, including BRF1 (TFIIIB70) and GCN5 genes. Yeast. 13(4):373-377, 1997.

Marcus et al., Functional similarity and physical association between GCN5 and ADA2: putative transcriptional adaptors. EMBO J. 13(20):4807-4815, 1994.

Mazzoni et al., Sequence analysis of a 10-5 kb DNA fragment from the yeast chromosome VII reveals the presence of three new open reading frames and of a tRNA$^{Thr}$ gene. Yeast. 13(4):369-372, 1997.

Adams, S. et al, "Fluorescence ratio imaging of cyclic AMP in single cells," *Nature* 349: 694-697, 1991.

Aitken, A. et al, "14-3-3 proteins: biological function and domain structure," *Biochemical Society Transactions*, 605-611, Received Mar. 3, 1995.

Baldwin, T. et al, "Cloning and Expression of the *lux*Y Gene from *Vibrio fischeri* Strain Y-1 in *Escherichia coli* and Complete Amino Acid Sequence of the Yellow Fluorescent Protein," *Biochemistry* 29: 5509-5515, 1990.

Cervoni, N. et al, "Demethylase Activity Is Directed by Histone Acetylation*," *Journal of Biological Chemistry* 276(44): 40778-70787, 2001.

Chen, I. et al, "Site-specific labeling of cell surface proteins with biophysical probes using biotin ligase," *Nature Methods* 2(2): 99-104, 2005.

Cubitt, A. et al, "Understanding, improving and using green fluorescent proteins," *Techniques TIBS* 20: 448-455, 1995.

González, J. et al, "Volatge Sensing by Fluorescence Resonance Energy Transfer in Single Cells," *Biophysical Journal* 69: 1272-1280, 1995.

Heim, R. et al, "Engineering green fluorescent protein for improved brightness, longer wavelengths and fluorescence resonance energy trasnfer," *Current Biology* 6: 178-182, 1996.

Heim, R. et al, "Wavelength mutations and posttranslational autoxidation of green fluorescent protein," *Proc. Natl. Acad. Sci. USA* 91: 12501-12504, 1994.

Herman, B. "Resonance Transfer Microscopy," *Methods in Cell Biology, Chapter 8* vol. 30: 219-243, 1989.

Huston, J. et al, "Protein engineering of antibody binding sites: Recovery of specific activity in an anti-digoxin single-chain Fv analogue produced in *Escherichia coli,"* *Proc. Natl. Acad. Sci. USA* 85: 5879-5883, 1988.

Levine, L. et al, "Isolation and Characterization of a Photoprotein, "Phialidin," and A Spectally Unique Green-Fluorescent Protein from the Bioluminescent Jellyfish Phialidium Gregarium*," *Comp. Biochem. Physiol.* 72B: 77-85, 1982.

Li, L. et al, "Continuous Fluorescence Assay of Phytochrome Assembly *in Vitro,"* *Biochemistry* 34: 7923-7930, 1995.

Meijsing, S. et al, "The silencing complex SAS-I lings histone acetylation to the assembly of repressed chromatin by CAF-I and Asfl in *Saccharomyces cerevisiae,"* *Genes & Development* 15: 3169-3182, 2001.

Newton, D. et al, "Angiogenin Single-Chain Immunofusions: Influence of Peptide Liners and Spacers between Fusion Protein Domains," *Biochemistry* 35: 545-553, 1996.

Norris, B. et al, "Nucleotide sequence of a cDNA clone encoding the precursor of the peridinin-chlorophyll *a*-binding proetin from the dinoflagellate *Symbiodinium* sp.," *Plant Molecular Biology* 24: 673-677, 1994.

Prasher, D. et al, "Primary structure of the *Aequorea victoria* green-fluorescent protein," *Gene* 111: 229-233, 1992.

Rundlett, S. et al, "HDA1 and RPD3 are members of distinct yeast histone deacetylase complexes that regulate silencing and transcription," *Proc. Natl. Acad. Sci. USA* 93: 14503-14508, 1986.

Singal, R. et al, "Methylation of a-type embryonic globin gene *a*πrepresses transcription in primary erythroid cells," *Blood* 2002 (abstract).

Tsukamoto, T. et al, "Visualization of gene activity in living cells," Nature Cell Biology 2: 871-878, 2000.

Ward, W. et al, "Spectral Perturbations of the *AEQUOREA* Green-Fluorescent Protein," Photochem. Photobiol. 35: 803-808, 1982.

Whitlow, M. et al, "An improved linker for single-chain Fv with reduced aggregation and enhanced proteolytic stability," *Protein Engineering* 6(8): 989-995, 1993.

Wilbanks, S. et al, "Rod Structure of a Phycoerythrin II-containing Phycobilisome," *Journal of Biological Chemistry* 268(2): 1226-1993, 1993.

Lin, C. et al., "Genetically Encoded Fluorescent Reporters of Histone Methylation in Living Cells," *J. Am. Chem. Soc.*, 126:5982-3, 2004.

Lin, C. et al., "A Genetically Encoded Fluorescent Reporter of Histone Phosphorylation in Living Cells," *Angew. Chem Int. Ed.*, 43:2940-3, 2004.

* cited by examiner

SEQUENCE LISTING

<160> NUMBER OF SEQ ID NOS: 22

<210> SEQ ID NO 1
<211> LENGTH: 40
<212> TYPE: PRT
<213> ORGANISM: Homo sapiens

<400> SEQUENCE: 1

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ala Thr
            20                  25                  30

Gly Gly Val Lys Lys Pro His Arg
        35                  40

<210> SEQ ID NO 2
<211> LENGTH: 30
<212> TYPE: PRT
<213> ORGANISM: Homo sapiens

<400> SEQUENCE: 2

Ser Gly Arg Gly Lys Gly Gly Lys Gly Leu Gly Lys Gly Gly Ala Lys
1               5                   10                  15

Arg His Arg Lys Val Leu Arg Asp Asn Ile Gln Gly Ile Thr
            20                  25                  30

<210> SEQ ID NO 3
<211> LENGTH: 109
<212> TYPE: PRT
<213> ORGANISM: Saccharomyces cerevisiae

<400> SEQUENCE: 3

Arg Gly Pro His Asp Ala Ala Ile Gln Asn Ile Leu Thr Glu Leu Gln
1               5                   10                  15

Asn His Ala Ala Ala Trp Pro Phe Leu Gln Pro Val Asn Lys Glu Glu
                20                  25                  30

Val Pro Asp Tyr Tyr Asp Phe Ile Lys Glu Pro Met Asp Leu Ser Thr
                35                  40                  45

Met Glu Ile Lys Leu Glu Asn Lys Tyr Gln Lys Met Glu Asp Phe Ile
        50                  55                  60

Tyr Asp Ala Arg Leu Val Phe Asn Asn Cys Arg Met Tyr Asn Gly Glu
65              70                  75                  80

Asn Thr Ser Tyr Tyr Lys Tyr Ala Asn Arg Leu Glu Lys Phe Phe Asn
                85                  90                  95

Asn Lys Val Lys Glu Ile Pro Glu Tyr Ser Leu Ile Asp
            100                 105

```
<210> SEQ ID NO 4
<211> LENGTH: 1908
<212> TYPE: DNA
<213> ORGANISM: Saccharomyces cerevisiae

<400> SEQUENCE: 4
```

| | | | | |
|---|---|---|---|---|
| aagcttgcgg | ccgccaccat | ggtgagcaag | ggcgaggagc | tgttcaccgg | ggtggtgccc | 60 |
| atcctggtcg | agctggacgg | cgacgtaaac | ggccacaggt | tcagcgtgtc | cggcgagggc | 120 |
| gagggcgatg | ccacctacgg | caagctgacc | ctgaagttca | tctgcaccac | cggcaagctg | 180 |
| cccgtgccct | ggcccaccct | cgtgaccacc | ctgacctggg | gcgtgcagtg | cttcagccgc | 240 |
| taccccgacc | acatgaagca | gcacgacttc | ttcaagtccg | ccatgcccga | aggctacgtc | 300 |
| caggagcgta | ccatcttctt | caaggacgac | ggcaactaca | agacccgcgc | cgaggtgaag | 360 |
| ttcgagggcg | acaccctggt | gaaccgcatc | gagctgaagg | gcatcgactt | caaggaggac | 420 |
| ggcaacatcc | tggggcacaa | gctggagtac | aactacatca | gccacaacgt | ctatatcacc | 480 |
| gccgacaagc | agaagaacgg | catcaaggcc | cacttcaaga | tccgccacaa | catcgaggac | 540 |
| ggcagcgtgc | agctcgccga | ccactaccag | cagaacaccc | ccatcggcga | cggccccgtg | 600 |
| ctgctgcccg | acaaccacta | cctgagcacc | cagtccgccc | tgagcaaaga | ccccaacgag | 660 |
| aagcgcgatc | acatggtcct | gctggagttc | gtgaccgccg | ccgcatgca | taagcgtggt | 720 |
| ccacacgatg | cagcaataca | gaatatactc | acagagctac | aaaatcatgc | agcagcttgg | 780 |
| cccttcttac | aacccgttaa | taagaggag | gtccccgact | attatgattt | tatcaaagag | 840 |
| ccaatggact | tgagcaccat | ggaaataaaa | ttagagagca | acaaatatca | gaagatggaa | 900 |
| gacttcatat | atgatgccag | attggtgttt | aacaattgcc | gaatgtacaa | tggcgagaat | 960 |
| acgtcgtatt | acaagtatgc | taataggcta | gagaaattct | tcaataataa | agtaaaagaa | 1020 |
| atacctgaat | attctcacct | tattgatggg | tctacatctg | gatctgggaa | gccgggttct | 1080 |
| ggtgagggtt | cttctggtcg | cggcaaaggc | ggtaaaggtt | tgggtaaggg | aggtgccaag | 1140 |
| cgtcaccgaa | aagtgctgcg | ggataacatc | caaggcatca | ccgagctcat | ggtgagcaag | 1200 |
| ggcgaggagc | tgttcaccgg | ggtggtgccc | atcctggtcg | agctggacgg | cgacgtaaac | 1260 |
| ggccacaagt | tcagcgtgtc | cggcgagggc | gagggcgatg | ccacctacgg | caagctgacc | 1320 |
| ctgaagttca | tctgcaccac | cggcaagctg | cccgtgccct | ggcccaccct | cgtgaccacc | 1380 |
| ttcggctacg | gcctgatgtg | cttcgcccgc | taccccgacc | acatgaagca | gcacgacttc | 1440 |
| ttcaagtccg | ccatgcccga | aggctacgtc | caggagcgca | ccatcttctt | caaggacgac | 1500 |

```
ggcaactaca agacccgcgc cgaggtgaag ttcgagggcg acaccctggt gaaccgcatc    1560
gagctgaagg gcatcgactt caaggaggac ggcaacatcc tggggcacaa gctggagtac    1620
aactacaaca gccacaacgt ctatatcatg gccgacaagc agaagaacgg catcaaggtg    1680
aacttcaaga tccgccacaa catcgaggac ggcagcgtgc agctcgccga ccactaccag    1740
cagaacaccc ccatcggcga cggccccgtg ctgctgcccg acaaccacta cctgagctac    1800
cagtccgccc tgagcaaaga ccccaacgag aagcgcgatc acatggtcct gctggagttc    1860
gtgaccgccg ccgggatcac tctcggcatg gacgagctgt acaagtaa                1908
```

<210> SEQ ID NO 5
<211> LENGTH: 635
<212> TYPE: PRT
<213> ORGANISM: Saccharomyces cerevisiae

<400> SEQUENCE: 5

```
Lys Leu Ala Ala Ala Thr Met Val Ser Lys Gly Glu Glu Leu Phe Thr
1               5                   10                  15

Gly Val Val Pro Ile Leu Val Glu Leu Asp Gly Asp Val Asn Gly His
            20                  25                  30

Arg Phe Ser Val Ser Gly Glu Gly Glu Gly Asp Ala Thr Tyr Gly Lys
        35                  40                  45

Leu Thr Leu Lys Phe Ile Cys Thr Thr Gly Lys Leu Pro Val Pro Trp
    50                  55                  60

Pro Thr Leu Val Thr Thr Leu Thr Trp Gly Val Gln Cys Phe Ser Arg
65                  70                  75                  80

Tyr Pro Asp His Met Lys Gln His Asp Phe Phe Lys Ser Ala Met Pro
                85                  90                  95

Glu Gly Tyr Val Gln Glu Arg Thr Ile Phe Phe Lys Asp Asp Gly Asn
            100                 105                 110

Tyr Lys Thr Arg Ala Glu Val Lys Phe Glu Gly Asp Thr Leu Val Asn
        115                 120                 125

Arg Ile Glu Leu Lys Gly Ile Asp Phe Lys Glu Asp Gly Asn Ile Leu
    130                 135                 140

Gly His Lys Leu Glu Tyr Asn Tyr Ile Ser His Asn Val Tyr Ile Thr
145                 150                 155                 160

Ala Asp Lys Gln Lys Asn Gly Ile Lys Ala His Phe Lys Ile Arg His
                165                 170                 175

Asn Ile Glu Asp Gly Ser Val Gln Leu Ala Asp His Tyr Gln Gln Asn
            180                 185                 190

Thr Pro Ile Gly Asp Gly Pro Val Leu Leu Pro Asp Asn His Tyr Leu
        195                 200                 205

Ser Thr Gln Ser Ala Leu Ser Lys Asp Pro Asn Glu Lys Arg Asp His
    210                 215                 220

Met Val Leu Leu Glu Phe Val Thr Ala Ala Arg Met His Lys Arg Gly
225                 230                 235                 240

Pro His Asp Ala Ala Ile Gln Asn Ile Leu Thr Glu Leu Gln Asn His
                245                 250                 255

Ala Ala Ala Trp Pro Phe Leu Gln Pro Val Asn Lys Glu Glu Val Pro
            260                 265                 270

Asp Tyr Tyr Asp Phe Ile Lys Glu Pro Met Asp Leu Ser Thr Met Glu
        275                 280                 285

Ile Lys Leu Glu Ser Asn Lys Tyr Gln Lys Met Glu Asp Phe Ile Tyr
    290                 295                 300
```

```
Asp Ala Arg Leu Val Phe Asn Asn Cys Arg Met Tyr Asn Gly Glu Asn
305                 310                 315                 320

Thr Ser Tyr Tyr Lys Tyr Ala Asn Arg Leu Glu Lys Phe Phe Asn Asn
            325                 330                 335

Lys Val Lys Glu Ile Pro Glu Tyr Ser His Leu Ile Asp Gly Ser Thr
        340                 345                 350

Ser Gly Ser Gly Lys Pro Gly Ser Gly Glu Gly Ser Ser Gly Arg Gly
    355                 360                 365

Lys Gly Gly Lys Gly Leu Gly Lys Gly Gly Ala Lys Arg His Arg Lys
370                 375                 380

Val Leu Arg Asp Asn Ile Gln Gly Ile Thr Glu Leu Met Val Ser Lys
385                 390                 395                 400

Gly Glu Glu Leu Phe Thr Gly Val Val Pro Ile Leu Val Glu Leu Asp
                405                 410                 415

Gly Asp Val Asn Gly His Lys Phe Ser Val Ser Gly Glu Gly Glu Gly
            420                 425                 430

Asp Ala Thr Tyr Gly Lys Leu Thr Leu Lys Phe Ile Cys Thr Thr Gly
        435                 440                 445

Lys Leu Pro Val Pro Trp Pro Thr Leu Val Thr Thr Phe Gly Tyr Gly
    450                 455                 460

Leu Met Cys Phe Ala Arg Tyr Pro Asp His Met Lys Gln His Asp Phe
465                 470                 475                 480

Phe Lys Ser Ala Met Pro Glu Gly Tyr Val Gln Glu Arg Thr Ile Phe
                485                 490                 495

Phe Lys Asp Asp Gly Asn Tyr Lys Thr Arg Ala Glu Val Lys Phe Glu
            500                 505                 510

Gly Asp Thr Leu Val Asn Arg Ile Glu Leu Lys Gly Ile Asp Phe Lys
        515                 520                 525

Glu Asp Gly Asn Ile Leu Gly His Lys Leu Glu Tyr Asn Tyr Asn Ser
    530                 535                 540

His Asn Val Tyr Ile Met Ala Asp Lys Gln Lys Asn Gly Ile Lys Val
545                 550                 555                 560

Asn Phe Lys Ile Arg His Asn Ile Glu Asp Gly Ser Val Gln Leu Ala
                565                 570                 575

Asp His Tyr Gln Gln Asn Thr Pro Ile Gly Asp Gly Pro Val Leu Leu
            580                 585                 590

Pro Asp Asn His Tyr Leu Ser Tyr Gln Ser Ala Leu Ser Lys Asp Pro
        595                 600                 605

Asn Glu Lys Arg Asp His Met Val Leu Leu Glu Phe Val Thr Ala Ala
    610                 615                 620

Gly Ile Thr Leu Gly Met Asp Glu Leu Tyr Lys
625                 630                 635

<210> SEQ ID NO 6
<211> LENGTH: 2412
<212> TYPE: DNA
<213> ORGANISM: Drosophila melanogaster

<400> SEQUENCE: 6
aagcttgcgg ccgccaccat ggtgagcaag ggcgaggagc tgttcaccgg ggtggtgccc    60
atcctggtcg agctggacgg cgacgtaaac ggccacaggt tcagcgtgtc cggcgagggc   120
gagggcgatg ccacctacgg caagctgacc ctgaagttca tctgcaccac cggcaagctg   180
cccgtgccct ggcccaccct cgtgaccacc ctgacctggg gcgtgcagtg cttcagccgc   240
```

-continued

```
tacccccgacc acatgaagca gcacgacttc ttcaagtccg ccatgcccga aggctacgtc      300
caggagcgta ccatcttctt caaggacgac ggcaactaca agacccgcgc cgaggtgaag      360
ttcgagggcg acaccctggt gaaccgcatc gagctgaagg gcatcgactt caaggaggac      420
ggcaacatcc tggggcacaa gctggagtac aactacatca gccacaacgt ctatatcacc      480
gccgacaagc agaagaacgg catcaaggcc cacttcaaga tccgccacaa catcgaggac      540
ggcagcgtgc agctcgccga ccactaccag cagaacaccc ccatcggcga cggccccgtg      600
ctgctgcccg acaaccacta cctgagcacc cagtccgccc tgagcaaaga ccccaacgag      660
aagcgcgatc acatggtcct gctggagttc gtgaccgccg cccgcatgca tggaaccact      720
gttcactgtg actatttgaa tagacctcat aagtccatcc accggcgccg cacagaccct      780
atggtgacgc tgtcgtccat cttggagtct atcatcaatg acatgagaga tcttccaaat      840 acatacccctt tccacactcc agtcaatgca aaggttgtaa aggactacta caaaatcatc      900
actcggccaa tggacctaca aacactccgc gaaaacgtgc gtaaacgcct ctacccatct      960
cgggaagagt tcagagagca tctgaagcta attgtgaaaa atagtgcaac ctacaatggg     1020
ccaaaacact cattgactca gatctctcaa tccatgctgg atctctgtga tgaaaaactc     1080
aaagagaaag aagacaaatt agctcgctta gagaaagcta tcaaccccctt gctggatgat     1140 gatgaccaag tggcgttttc tttcattctg gacaacattg tcacccagaa aatgatggca     1200
gttccagatt cttggccatt tcatcaccca gttaataaga aatttgttcc agattattac     1260
aaagtgattg tcaatccaat ggatttagag accatacgta gaacatctc caagcacaag     1320 tatcagagtc gggagagctt tctggatgat gtaaaccctta ttctggccaa cagtgttaag     1380
tataatggac ctgagagtca gtatactaag actgcccagg agattgtgaa cgtctgttac     1440
cagacattga ctgagtatga tgaacatttg actcaacttg agaaggatat ttgtactgct     1500
aaagaagcag ctttggagga agcagaatta gaaagcctgg acccaatgac cgggtctaca     1560
tctggatctg ggaagccggg ttctggtgag ggttcttctg gtcgcggcaa aggcggtaaa     1620
ggtttgggta agggaggtgc caagcgtcac cgaaaagtgc tgcgggataa catccaaggc     1680
atcaccgagc tcatggtgag caagggcgag gagctgttca ccggggtggt gcccatcctg     1740
gtcgagctgg acggcgacgt aaacggccac aagttcagcg tgtccggcga gggcgagggc     1800
gatgccacct acggcaagct gaccctgaag ttcatctgca ccaccggcaa gctgcccgtg     1860 cccctggccca ccctcgtgac caccttcggc tacggcctga tgtgcttcgc ccgctacccc     1920
gaccacatga agcagcacga cttcttcaag tccgccatgc ccgaaggcta cgtccaggag     1980
cgcaccatct tcttcaagga cgacggcaac tacaagaccc gcgccgaggt gaagttcgag     2040
ggcgacaccc tggtgaaccg catcgagctg aagggcatcg acttcaagga ggacggcaac     2100 atcctgggc acaagctgga gtacaactac aacagccaca cgtctatat catgccgac     2160 aagcagaaga acggcatcaa ggtgaacttc aagatccgcc acaacatcga ggacggcagc     2220
gtgcagctcg ccgaccacta ccagcagaac acccccatcg cgacggccc cgtgctgctg     2280 cccgacaacc actacctgag ctaccagtcc gccctgagca aagaccccaa cgagaagcgc     2340
gatcacatgg tcctgctgga gttcgtgacc gccgccggga tcactctcgg catggacgag     2400
ctgtacaagt aa                                                          2412
```

<210> SEQ ID NO 7
<211> LENGTH: 803
<212> TYPE: PRT

<213> ORGANISM: Drosophila melanogaster

<400> SEQUENCE: 7

```
Lys Leu Ala Ala Thr Met Val Ser Lys Gly Glu Leu Phe Thr
1               5                   10                  15
Gly Val Val Pro Ile Leu Val Glu Leu Asp Gly Asp Val Asn Gly His
                20                  25                  30
Arg Phe Ser Val Ser Gly Glu Gly Gly Asp Ala Thr Tyr Gly Lys
            35                  40                  45
Leu Thr Leu Lys Phe Ile Cys Thr Thr Gly Lys Leu Pro Val Pro Trp
50                  55                  60
Pro Thr Leu Val Thr Thr Leu Thr Trp Gly Val Gln Cys Phe Ser Arg
65                  70                  75                  80
Tyr Pro Asp His Met Lys Gln His Asp Phe Phe Lys Ser Ala Met Pro
                85                  90                  95
Glu Gly Tyr Val Gln Glu Arg Thr Ile Phe Phe Lys Asp Asp Gly Asn
            100                 105                 110
Tyr Lys Thr Arg Ala Glu Val Lys Phe Glu Gly Asp Thr Leu Val Asn
        115                 120                 125
Arg Ile Glu Leu Lys Gly Ile Asp Phe Lys Glu Asp Gly Asn Ile Leu
    130                 135                 140
Gly His Lys Leu Glu Tyr Asn Tyr Ile Ser His Asn Val Tyr Ile Thr
145                 150                 155                 160
Ala Asp Lys Gln Lys Asn Gly Ile Lys Ala His Phe Lys Ile Arg His
                165                 170                 175
Asn Ile Glu Asp Gly Ser Val Gln Leu Ala Asp His Tyr Gln Gln Asn
            180                 185                 190
Thr Pro Ile Gly Asp Gly Pro Val Leu Leu Pro Asp Asn His Tyr Leu
        195                 200                 205
Ser Thr Gln Ser Ala Leu Ser Lys Asp Pro Asn Glu Lys Arg Asp His
    210                 215                 220
Met Val Leu Leu Glu Phe Val Thr Ala Ala Arg Met His Gly Thr Thr
225                 230                 235                 240
Val His Cys Asp Tyr Leu Asn Arg Pro His Lys Ser Ile His Arg Arg
                245                 250                 255
Arg Thr Asp Pro Met Val Thr Leu Ser Ser Ile Leu Glu Ser Ile Ile
            260                 265                 270
Asn Asp Met Arg Asp Leu Pro Asn Thr Tyr Pro Phe His Thr Pro Val
        275                 280                 285
Asn Ala Lys Val Val Lys Asp Tyr Tyr Lys Ile Ile Thr Arg Pro Met
    290                 295                 300
Asp Leu Gln Thr Leu Arg Glu Asn Val Arg Lys Arg Leu Tyr Pro Ser
305                 310                 315                 320
Arg Glu Glu Phe Arg Glu His Leu Glu Leu Ile Val Lys Asn Ser Ala
                325                 330                 335
Thr Tyr Asn Gly Pro Lys His Ser Leu Thr Gln Ile Ser Gln Ser Met
            340                 345                 350
Leu Asp Leu Cys Asp Glu Lys Leu Lys Glu Lys Glu Asp Lys Leu Ala
        355                 360                 365
Arg Leu Glu Lys Ala Ile Asn Pro Leu Leu Asp Asp Asp Gln Val
    370                 375                 380
Ala Phe Ser Phe Ile Leu Asp Asn Ile Val Thr Gln Lys Met Met Ala
385                 390                 395                 400
```

-continued

```
Val Pro Asp Ser Trp Pro Phe His Pro Val Asn Lys Lys Phe Val
            405                 410                 415

Pro Asp Tyr Tyr Lys Val Ile Val Asn Pro Met Asp Leu Glu Thr Ile
        420                 425                 430

Arg Lys Asn Ile Ser Lys His Lys Tyr Gln Ser Arg Glu Ser Phe Leu
            435                 440                 445

Asp Asp Val Asn Leu Ile Leu Ala Asn Ser Val Lys Tyr Asn Gly Pro
450                 455                 460

Glu Ser Gln Tyr Thr Lys Thr Ala Gln Glu Ile Val Asn Val Cys Tyr
465                 470                 475                 480

Gln Thr Leu Thr Glu Tyr Asp Glu His Leu Thr Gln Leu Glu Lys Asp
                485                 490                 495

Ile Cys Thr Ala Lys Glu Ala Ala Leu Glu Glu Ala Glu Leu Glu Ser
            500                 505                 510

Leu Asp Pro Met Thr Gly Ser Thr Ser Gly Ser Gly Lys Pro Gly Ser
            515                 520                 525

Gly Glu Gly Ser Ser Gly Arg Gly Lys Gly Lys Gly Leu Gly Lys
530                 535                 540

Gly Gly Ala Lys Arg His Arg Lys Val Leu Arg Asp Asn Ile Gln Gly
545                 550                 555                 560

Ile Thr Glu Leu Met Val Ser Lys Gly Glu Glu Leu Phe Thr Gly Val
                565                 570                 575

Val Pro Ile Leu Val Glu Leu Asp Gly Asp Val Asn Gly His Lys Phe
            580                 585                 590

Ser Val Ser Gly Glu Gly Glu Gly Asp Ala Thr Tyr Gly Lys Leu Thr
            595                 600                 605

Leu Lys Phe Ile Cys Thr Thr Gly Lys Leu Pro Val Pro Trp Pro Thr
610                 615                 620

Leu Val Thr Thr Phe Gly Tyr Gly Leu Met Cys Phe Ala Arg Tyr Pro
625                 630                 635                 640

Asp His Met Lys Gln His Asp Phe Phe Lys Ser Ala Met Pro Glu Gly
                645                 650                 655

Tyr Val Gln Glu Arg Thr Ile Phe Phe Lys Asp Asp Gly Asn Tyr Lys
            660                 665                 670

Thr Arg Ala Glu Val Lys Phe Glu Gly Asp Thr Leu Val Asn Arg Ile
            675                 680                 685

Glu Leu Lys Gly Ile Asp Phe Lys Glu Asp Gly Asn Ile Leu Gly His
690                 695                 700

Lys Leu Glu Tyr Asn Tyr Asn Ser His Asn Val Tyr Ile Met Ala Asp
705                 710                 715                 720

Lys Gln Lys Asn Gly Ile Lys Val Asn Phe Lys Ile Arg His Asn Ile
                725                 730                 735

Glu Asp Gly Ser Val Gln Leu Ala Asp His Tyr Gln Gln Asn Thr Pro
            740                 745                 750

Ile Gly Asp Gly Pro Val Leu Leu Pro Asp Asn His Tyr Leu Ser Tyr
            755                 760                 765

Gln Ser Ala Leu Ser Lys Asp Pro Asn Glu Lys Arg Asp His Met Val
770                 775                 780

Leu Leu Glu Phe Val Thr Ala Ala Gly Ile Thr Leu Gly Met Asp Glu
785                 790                 795                 800

Leu Tyr Lys
```

<210> SEQ ID NO 8

```
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 8

Gly Gly Gly Gly Ser Gly Gly Gly Gly Ser
1               5                   10

<210> SEQ ID NO 9
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 9

Gly Lys Ser Ser Gly Ser Gly Ser Glu Ser Lys Ser
1               5                   10

<210> SEQ ID NO 10
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 10

Gly Ser Thr Ser Gly Ser Gly Lys Ser Ser Glu Gly Lys Gly
1               5                   10

<210> SEQ ID NO 11
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 11

Gly Ser Thr Ser Gly Ser Gly Lys Ser Ser Glu Gly Ser Gly Ser Thr
1               5                   10                  15

Lys Gly

<210> SEQ ID NO 12
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 12

Gly Ser Thr Ser Gly Ser Gly Lys Ser Ser Glu Gly Lys Gly
1               5                   10

<210> SEQ ID NO 13
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 13

Gly Ser Thr Ser Gly Ser Gly Lys Pro Gly Ser Gly Glu Gly Ser Thr
1               5                   10                  15

Lys Gly
```

<210> SEQ ID NO 14
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 14

Glu Gly Lys Ser Ser Gly Ser Gly Ser Glu Ser Lys Glu Phe
1               5                   10

<210> SEQ ID NO 15
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 15

Ala Gly Gly Thr Gly Gly Ser Leu
1               5

<210> SEQ ID NO 16
<211> LENGTH: 34
<212> TYPE: PRT
<213> ORGANISM: Artificial sequence
<220> FEATURE:
<223> OTHER INFORMATION: Synthetic polypeptide

<400> SEQUENCE: 16

Gly Ser Thr Ser Gly Ser Gly Lys Pro Gly Ser Gly Glu Gly Ser Thr
1               5                   10                  15

Gly Ala Gly Gly Ala Gly Ser Thr Ser Gly Ser Gly Lys Pro Ser Gly
            20                  25                  30

Glu Gly

<210> SEQ ID NO 17
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 17

Gly Ser Thr Ser Gly Ser Gly Lys Pro Gly Ser Gly Glu Gly Ser
1               5                   10                  15

<210> SEQ ID NO 18
<211> LENGTH: 30
<212> TYPE: PRT
<213> ORGANISM: Homo sapiens

<400> SEQUENCE: 18

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro
            20                  25                  30

<210> SEQ ID NO 19
<211> LENGTH: 15
<212> TYPE: PRT
<213> ORGANISM: Artificial sequence
<220> FEATURE:
<223> OTHER INFORMATION: Synthetic polypeptide

```
<400> SEQUENCE: 19

Gly Gly Gly Gly Ser Gly Gly Gly Ser Gly Gly Gly Ser
1               5                   10                  15

<210> SEQ ID NO 20
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 20

Gly Gly Gly Gly Ser Gly Gly Gly Ser Gly Gly Gly Gly Ser Gly
1               5                   10                  15

Gly Gly Gly Ser
            20

<210> SEQ ID NO 21
<211> LENGTH: 25
<212> TYPE: PRT
<213> ORGANISM: Artificial sequence
<220> FEATURE:
<223> OTHER INFORMATION: Synthetic polypeptide

<400> SEQUENCE: 21

Gly Gly Gly Gly Ser Gly Gly Gly Ser Gly Gly Gly Gly Ser Gly
1               5                   10                  15

Gly Gly Gly Ser Gly Gly Gly Gly Ser
            20                  25

<210> SEQ ID NO 22
<211> LENGTH: 30
<212> TYPE: PRT
<213> ORGANISM: Artificial sequence
<220> FEATURE:
<223> OTHER INFORMATION: Synthetic polypeptide

<400> SEQUENCE: 22

Gly Gly Gly Gly Ser Gly Gly Gly Gly Ser Gly Gly Gly Ser Gly
1               5                   10                  15

Gly Gly Gly Ser Gly Gly Gly Gly Ser Gly Gly Gly Gly Ser
            20                  25                  30
```

US 7,056,683 B2

GENETICALLY ENCODED FLUORESCENT REPORTERS OF KINASE, METHYLTRANSFERASE, AND ACETYL-TRANSFERASE ACTIVITIES

RELATED APPLICATIONS

This application claims priority under 35 U.S.C. §119 to U.S. provisional application Ser. No. 60/425,578, filed Nov. 12, 2002.

GOVERNMENT SUPPORT

This invention was made with government support under Grant Number N00014-03-1-0456 awarded by the Navy. The government has certain rights in the invention.

FIELD OF THE INVENTION

The invention relates to products and methods of making and using fusion protein reporters to monitor histone modification, such as acetylation, methylation, and phosphorylation. The invention relates to the use of fusion protein reporters in methods and compositions for the diagnosis and evaluation of histone modification-associated disorders.

BACKGROUND OF THE INVENTION

Recent advances in protein engineering, chemistry, and fluorescence microscopy have resulted in improved quantitative reporters of signaling events in living cells (Zhang, J. et al., *Nat. Rev. Mol. Cell. Biol.*, 2002, 3(12):906–18). For example, the engineering of spectrum-altered fluorescent proteins (FPs) from the *Aequorea victoria* Green Fluorescent Protein (GFP) has enabled simultaneous real-time measurement of multiple protein expression and localization patterns in live cells. FP-based indicators are less toxic than simple organic dyes and can respond to a wider range of biological events; they can also be targeted to subcellular compartments through genetic fusion and can be introduced into a wider variety of tissues and into intact organisms.

Although great strides have been made in FP-based indicator development, there are drawbacks in the existing technology. Existing indicators have been designed on a "custom cut", one-at-a-time basis. They are thus currently capable of reporting only a handful of the thousands of cellular signaling state variables. Additionally, few existing FP indicators have been developed to report on the more complex cellular parameters such as enzyme activity. These "hidden" variables are implicated in every known signaling pathway, but their direct observation has not been effectively addressed by current methodology.

SUMMARY OF THE INVENTION

The invention includes fusion protein reporters that may be used to monitor the modification of proteins (e.g. histones) in cells, including real-time monitoring of protein (e.g. histone) modification in living cells. Use of these novel reporters allows the determination of the level of modification of proteins, for example histones, including the level of acetylation, methylation, and phosphorylation. These determinations can be compared to control levels and thus allow diagnosis of disorders that are associated with levels of protein (e.g. histone) modification that differ from normal levels. The reporters can also be used to evaluate candidate pharmaceutical agents for use in prevention and/or treatment of protein modification-associated disorders, for example histone-modification-associated disorders. These evaluations can be done in cells, tissues, samples, or in subjects to determine the effect of pharmaceutical agents on the level of protein (e.g. histone modification. In addition, the fusion protein reporters of the invention can be utilized in non-invasive methods to assess cellular response to external stimuli.

According to one aspect of the invention, fusion protein reporters are provided. The fusion proteins include a core comprising a histone-modification-specific binding domain conjugated to a histone polypeptide substrate, wherein the core is flanked by donor and acceptor fluorescent moieties. In some embodiments, the histone modification specific binding domain is conjugated to the histone polypeptide substrate with a linker molecule. In certain embodiments, the fusion protein reporter also includes one or more additional histone-modification-specific binding domains. In some embodiments, the histone polypeptide substrate is selected from the group consisting of H3 or H4. In some embodiments, the histone polypeptide is selected from the group consisting of the N-terminus of H3 and the N-terminus of H4. In some embodiments, the donor fluorescent moiety is selected from the group consisting of cyan fluorescent protein (CFP), enhanced cyan fluorescent protein (ECFP), and the A206K mutants of these proteins (non-dimerizing). In certain embodiments, the acceptor fluorescent moiety is selected from the group consisting of yellow fluorescent protein (YFP), enhanced yellow fluorescent protein (EYFP), Citrine, and Venus, and the A206K mutants of these proteins. In some embodiments, the histone modification is selected from the group consisting of acetylation, methylation, and phosphorylation. In some embodiments, the histone modification-specific binding domain is selected from the group consisting of: 14-3-3, FHA, WW, bromodomain, and chromodomain. In some embodiments, the bromodomain is selected from the group consisting of: Gcn5, $TAF_{II}250$, P/CAF, CBP, BRG1, Swi2, and Sth1. In some embodiments, the chromodomain is selected from the group consisting of: HP1, MRG15, MRG-1, cynCDY, Hrp3, dMi-2, CHD5, Swi6, and pdd3p. In certain embodiments, the bromodomain comprises the amino acid sequence set forth as SEQ ID NO: 3. In some embodiments, the histone polypeptide is a polypeptide substrate for the histone-modification-specific binding domain. In certain embodiments, the histone polypeptide is an H3 polypeptide comprising the amino acid sequence set forth as ARTKQTARKSTG-GKAPRKQLATKAARKSAPATGGVKKPHR (SEQ ID NO:1). In certain embodiments, the histone polypeptide is an H3 polypeptide comprising the amino acid sequence set forth as ARTKQTARKSTGGKAPRKQLATKAARKSAP (SEQ ID NO: 18). In other embodiments, the histone polypeptide is an H4 polypeptide comprising the amino acid sequence set forth as SGRGKGGKGLGKGGAKRHRKV-LRDNIQGIT (SEQ ID NO:2). In certain embodiments, the fusion protein reporter also includes a targeting polypeptide, associated with the fusion protein. In some embodiments, the targeting polypeptide is selected from the group consisting of a receptor ligand and a nuclear localization sequence (NLS), nuclear export signal (NES), plasma membrane targeting signal, a histone binding protein, a histone protein and a nuclear protein.

In some aspects, the invention provides expression vectors comprising an expression cassette encoding a fusion protein reporter of any of the forgoing embodiments. Some aspects of the invention also provide host cell transformed or transfected with the expression vector.

According to another aspect of the invention, methods of determining the level of histone modification in a biological sample are provided. The methods include contacting a biological sample with a fusion protein reporter of any of the forgoing embodiments, and monitoring the level of fluorescence resonance energy transfer (FRET) in the biological sample as a measure of the level of histone modification in the biological sample. In some embodiments, the biological sample is a cell. In some embodiments, the cell is undergoing cell division.

According to yet another aspect of the invention, methods of monitoring the level of histone modification in a cell are provided. The methods include contacting a biological sample with a fusion protein reporter of any of the forgoing embodiments, determining a first level of fluorescence resonance energy transfer (FRET) in the biological sample, determining a second subsequent level of FRET in the biological sample, and comparing the first and second levels of FRET as a measure of the change in the level of histone modification in the biological sample. In some embodiments, the biological sample is a cell.

According to another aspect of the invention, methods of diagnosing a histone-modification disorder in a subject are provided. The methods include contacting a biological sample from a subject with a fusion protein reporter of any of the forgoing embodiments, monitoring the level of fluorescence resonance energy transfer (FRET) in the biological sample, comparing the level of FRET in the sample to a control level of FRET as a determination of a histone modification disorder in the subject. In some embodiments, the biological sample is selected from the group consisting of tissue and cells.

According to yet another aspect of the invention, methods of monitoring the onset, progression or regression of a histone-modification disorder in a subject are provided. The methods include contacting a first biological sample from a subject with a fusion protein reporter of any of the forgoing embodiments determining the level of fluorescence resonance energy transfer (FRET) in the first biological sample, contacting a subsequent second biological sample from the subject with a fusion protein reporter of any of for foregoing embodiments, determining the level of FRET in the second biological sample, comparing the level of FRET in the first biological sample to the level of FRET in the second biological sample as a measure of the onset, regression or progression of a histone modification disorder in the subject. In some embodiments, the biological sample is selected from the group consisting of tissue and cells.

In some embodiments, the method of monitoring the onset, progression or regression of a histone-modification disorder in a subject also includes administering after the first biological sample is obtained from the subject and before the second biological sample is obtained form the subject a candidate pharmacological agent to the subject, wherein the measure of the onset regression or progression of a histone modification disorder in the subject is an indication of the effect of the candidate pharmacological agent on histone modification in the subject.

According to another aspect of the invention, methods for evaluating the effect of a candidate pharmacological agent on histone modifications in a subject are provided. The methods include contacting a biological sample from the subject with a fusion protein reporter of any of the forgoing embodiments contacting the biological sample with a candidate pharmacological agent, monitoring the level of fluorescence resonance energy transfer (FRET) in the biological sample, comparing the level of FRET in the biological sample to the level of FRET in a control biological sample contacted with the fusion protein reporter and not contacted with the candidate pharmacological agent, wherein a relative increase or relative decrease in the level of FRET indicates an effect of the candidate pharmacological agent on histone modification in the subject.

According to another aspect of the invention, methods for evaluating the effect of candidate pharmacological agents on histone modification in a biological sample are provided. The methods include contacting a biological sample with a fusion protein reporter of any of the forgoing embodiments, determining a first level of fluorescence resonance energy transfer (FRET) in the biological sample, contacting the biological sample with a candidate pharmacological agent, determining a second level of FRET in the biological sample, and comparing the first level of FRET in the biological sample with the second level of FRET in the biological sample, wherein a relative increase or relative decrease in FRET indicates an effect of the candidate pharmacological agent on histone modification in the biological sample. In some embodiments the biological sample is a cell, tissue, or bodily fluid. In some embodiments, one of the biological samples is a control sample.

According to yet another aspect of the invention, kits for diagnosing a histone-modification disorder are provided. The kits include a fusion protein reporter of any of the forgoing embodiments, and instructions for the use of the fusion protein reporter in the diagnosis of a histone-modification disorder.

According to another aspect of the invention, methods for producing a fusion protein reporter are provided. The methods include providing an isolated nucleic acid molecule, wherein the isolated nucleic acid molecule is operably linked to a promoter encoding a fusion protein reporter comprising a core comprising a histone-modification-specific binding domain conjugated to a histone polypeptide, wherein the core is flanked by protein moieties, capable of being labeled with donor and acceptor fluorescent molecules, or a fragment thereof, and expressing the nucleic acid molecule in an expression system. In some embodiments, the method also includes isolating the fusion protein reporter or the fragment thereof from the expression system.

According to another aspect of the invention, fusion protein reporters are provided. The fusion protein reporters include a polypeptide encoded by a nucleic acid comprising a nucleotide sequence set forth as SEQ ID NO:4, wherein the fusion protein reporter is a yGcn5-based histone acetylation reporter. In some embodiments, the polypeptide comprises an amino acid sequence set forth as SEQ ID NO:5.

According to yet another aspect of the invention, fusion protein reporters are provided. The fusion protein reporters include a polypeptide encoded by a nucleic acid comprising a nucleotide sequence set forth as SEQ ID NO:6, wherein the fusion protein reporter is a TAFAB-based histone acetylation reporter. In some embodiments, the polypeptide comprises an amino acid sequence set forth as SEQ ID NO:7.

According to one aspect of the invention, fusion protein reporters are provided. The fusion proteins include a core comprising a post-translational-modification-specific binding domain conjugated to a polypeptide substrate, wherein the core is flanked by donor and acceptor fluorescent moieties. In some embodiments, the post-translational-modification-specific binding domain is a protein-modification binding domain. In some embodiments, the modification-specific binding domain is conjugated to the polypeptide substrate with a linker molecule. In certain embodiments, the fusion protein reporter also includes one or more additional modification-specific binding domains. In some embodiments, the polypeptide substrate includes all of the amino acid sequence or a fraction thereof of H2A, H2B, H3, or H4 from any species. In some embodiments, the donor fluorescent moiety is selected from the group consisting of cyan fluorescent protein (CFP), ECFP, and the A206K mutants of these proteins (non-dimerizing). In certain embodiments, the acceptor fluorescent moiety is selected from the group consisting of yellow fluorescent protein (YFP), EYFP, Citrine, and Venus, and the A206K mutants of these proteins. In some embodiments, the protein that is modified is a histone. In some embodiments, the protein that is modified is p53. In some embodiments, the protein that is modified is tubulin. In some embodiments, the protein modification is selected from the group consisting of acetylation, methylation, and phosphorylation. In some embodiments, the modification-specific binding domain is selected from the group consisting of: 14-3-3, FHA, WW, bromodomain, and chromodomain. In some embodiments, the bromodomain is selected from the group consisting of: Gcn5, $TAF_{II}250$, P/CAF, CBP, BRG1, Swi2, and Sth1. In some embodiments, the chromodomain is selected from the group consisting of: HP1, MRG15, MRG-1, cynCDY, Hrp3, dMi-2, CHD5, Swi6, and pdd3p. In certain embodiments, the bromodomain comprises the amino acid sequence set forth as SEQ ID NO: 3. In some embodiments, the histone polypeptide is a polypeptide substrate for the histone-modification-specific binding domain. In certain embodiments, the histone polypeptide is an H3 polypeptide comprising the amino acid sequence set forth as ARTKQTARKSTG-GKAPRKQLATKAARKSAPATGGVKKPHR (SEQ ID NO:1). In certain embodiments, the histone polypeptide is an H3 polypeptide comprising the amino acid sequence set forth as ARTKQTARKSTGGKAPRKQLATKAARKSAP (SEQ ID NO: 18). In other embodiments, the histone polypeptide is an H4 polypeptide comprising the amino acid sequence set forth as SGRGKGGKGLGKGGAKRHRKV-LRDNIQGIT (SEQ ID NO:2). In certain embodiments, the fusion protein reporter also includes a targeting polypeptide, associated with the fusion protein. In some embodiments, the targeting polypeptide is selected from the group consisting of a receptor ligand and a nuclear localization sequence (NLS), nuclear export signal (NES), plasma membrane targeting signal, a histone binding protein, p53, tubulin, a histone protein, and a nuclear protein.

In some aspects, the invention provides expression vectors comprising an expression cassette encoding a fusion protein reporter of any of the forgoing embodiments. Some aspects of the invention also provide host cell transformed or transfected with the expression vector.

According to another aspect of the invention, methods of determining the level of protein modification in a biological sample are provided. The methods include contacting a biological sample with a fusion protein reporter of any of the forgoing embodiments, and monitoring the level of fluorescence resonance energy transfer (FRET) in the biological sample as a measure of the level of protein modification in the biological sample. In some embodiments, the biological sample is a cell. In some embodiments, the cell is undergoing cell division.

According to yet another aspect of the invention, methods of monitoring the level of protein modification in a cell are provided. The methods include contacting a biological sample with a fusion protein reporter of any of the forgoing embodiments, determining a first level of fluorescence resonance energy transfer (FRET) in the biological sample, determining a second subsequent level of FRET in the biological sample, and comparing the first and second levels of FRET as a measure of the change in the level of protein modification in the biological sample. In some embodiments, the biological sample is a cell.

According to another aspect of the invention, methods of diagnosing a protein-modification disorder in a subject are provided. The methods include contacting a biological sample from a subject with a fusion protein reporter of any of the forgoing embodiments, monitoring the level of fluorescence resonance energy transfer (FRET) in the biological sample, comparing the level of FRET in the sample to a control level of FRET as a determination of a protein-modification disorder in the subject. In some embodiments, the biological sample is selected from the group consisting of tissue and cells.

According to yet another aspect of the invention, methods of monitoring the onset, progression or regression of a protein-modification disorder in a subject are provided. The methods include contacting a first biological sample from a subject with a fusion protein reporter of any of the forgoing embodiments determining the level of fluorescence resonance energy transfer (FRET) in the first biological sample, contacting a subsequent second biological sample from the subject with a fusion protein reporter of any of for foregoing embodiments, determining the level of FRET in the second biological sample, comparing the level of FRET in the first biological sample to the level of FRET in the second biological sample as a measure of the onset, regression or progression of a protein-modification disorder in the subject. In some embodiments, the biological sample is selected from the group consisting of tissue and cells.

In some embodiments, the method of monitoring the onset, progression or regression of a protein-modification disorder in a subject also includes administering after the first biological sample is obtained from the subject and before the second biological sample is obtained form the subject a candidate pharmacological agent to the subject, wherein the measure of the onset regression or progression of a protein-modification disorder in the subject is an indication of the effect of the candidate pharmacological agent on protein modification in the subject.

According to another aspect of the invention, methods for evaluating the effect of a candidate pharmacological agent on protein modifications in a subject are provided. The methods include contacting a biological sample from the subject with a fusion protein reporter of any of the forgoing embodiments contacting the biological sample with a candidate pharmacological agent, monitoring the level of fluorescence resonance energy transfer (FRET) in the biological sample, comparing the level of FRET in the biological sample to the level of FRET in a control biological sample contacted with the fusion protein reporter and not contacted with the candidate pharmacological agent, wherein a relative increase or relative decrease in the level of FRET indicates an effect of the candidate pharmacological agent on protein modification in the subject.

According to another aspect of the invention, methods for evaluating the effect of candidate pharmacological agents on protein modification in a biological sample are provided. The methods include contacting a biological sample with a fusion protein reporter of any of the forgoing embodiments, determining a first level of fluorescence resonance energy transfer (FRET) in the biological sample, contacting the biological sample with a candidate pharmacological agent, determining a second level of FRET in the biological sample, and comparing the first level of FRET in the biological sample with the second level of FRET in the biological sample, wherein a relative increase or relative decrease in FRET indicates an effect of the candidate pharmacological agent on protein modification in the biological sample. In some embodiments the biological sample is a cell, tissue, or bodily fluid. In some embodiments, one of the biological samples is a control sample.

According to yet another aspect of the invention, kits for diagnosing a protein-modification disorder are provided. The kits include a fusion protein reporter of any of the forgoing embodiments, and instructions for the use of the fusion protein reporter in the diagnosis of a protein-modification disorder.

According to another aspect of the invention, methods for producing a fusion protein reporter are provided. The methods include providing an isolated nucleic acid molecule, wherein the isolated nucleic acid molecule is operably linked to a promoter encoding a fusion protein reporter comprising a core comprising a protein-modification-specific binding domain conjugated to a substrate polypeptide, wherein the core is flanked by protein moieties, capable of being labeled with donor and acceptor fluorescent molecules, or a fragment thereof, and expressing the nucleic acid molecule in an expression system. In some embodiments, the method also includes isolating the fusion protein reporter or the fragment thereof from the expression system.

These and other aspects of the invention, as well as various embodiments thereof, will become more apparent in reference to the drawings and detailed description of the invention.

BRIEF DESCRIPTION OF THE DRAWINGS

The figures are illustrative only and are not required for enablement of the invention disclosed herein.

```
ARTKQTARKSTGGKAPRKQLATKAARKSAP     is SEQ ID NO:18
and
SGRGKGGKGLGKGGAKRHRKVLRDNIQGIT.    is SEQ ID NO:2
```

Figure 2A:
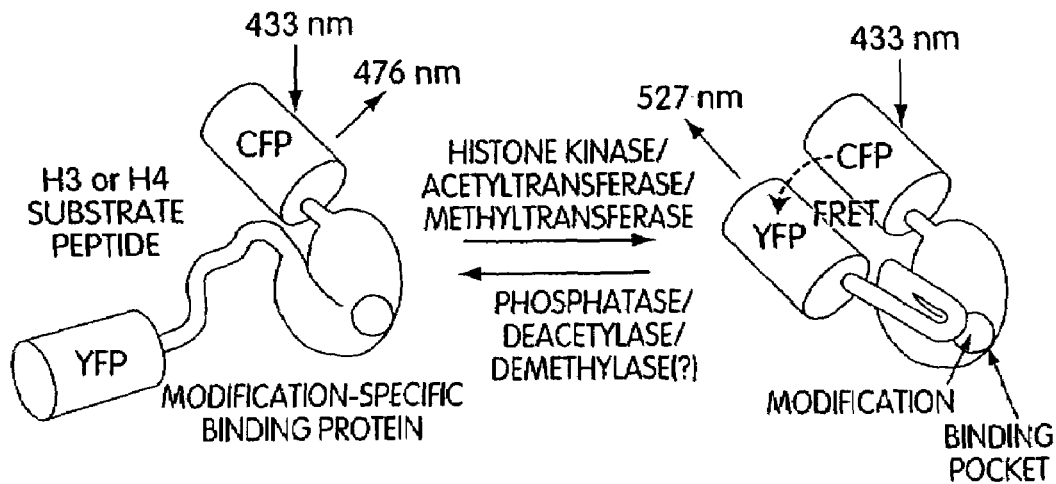
Figure 2B:
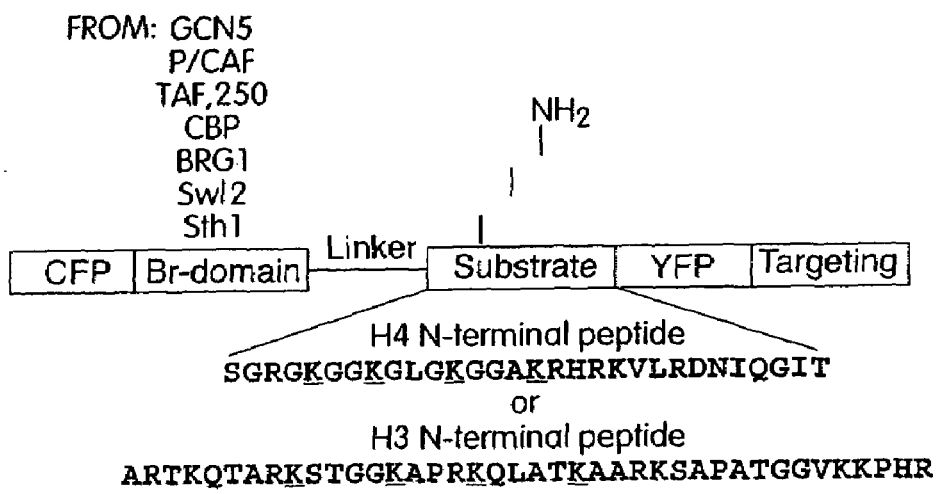

FIG. 2 shows a schematic design of a fusion protein reporter. FIG. 2A shows a general design of a FRET-based indicator of histone modification state in living cells. The modification-specific binding domain may be a 14-3-3 or FHA domain for detecting histone phosphorylation, a bromodomain for detecting acetylation, or a chromodomain for detecting methylation. FIG. 2B shows the domain structure of an indicator for detecting acetyltransferase activity. The bromodomain comes from one of several bromodomain-containing proteins. The substrate consists of either the H3 or H4 N-terminal peptide. The acetylation-competent lysines are underlined. The entire reporter can be fused to localization signals or specialized proteins for targeting to specific enzymes, DNA sequences, or chromatin regions. ARTKQTARKSTGGKAPRKQLATKAARK-SAPATGGVKKPHR is an H3 N-terminal peptide (SEQ ID NO:1) and SGRGKGGKGLGKGGAKRHRKVLRD-NIQGIT is an H4 N-terminal peptide (SEQ ID NO:2).

Figure 3A:
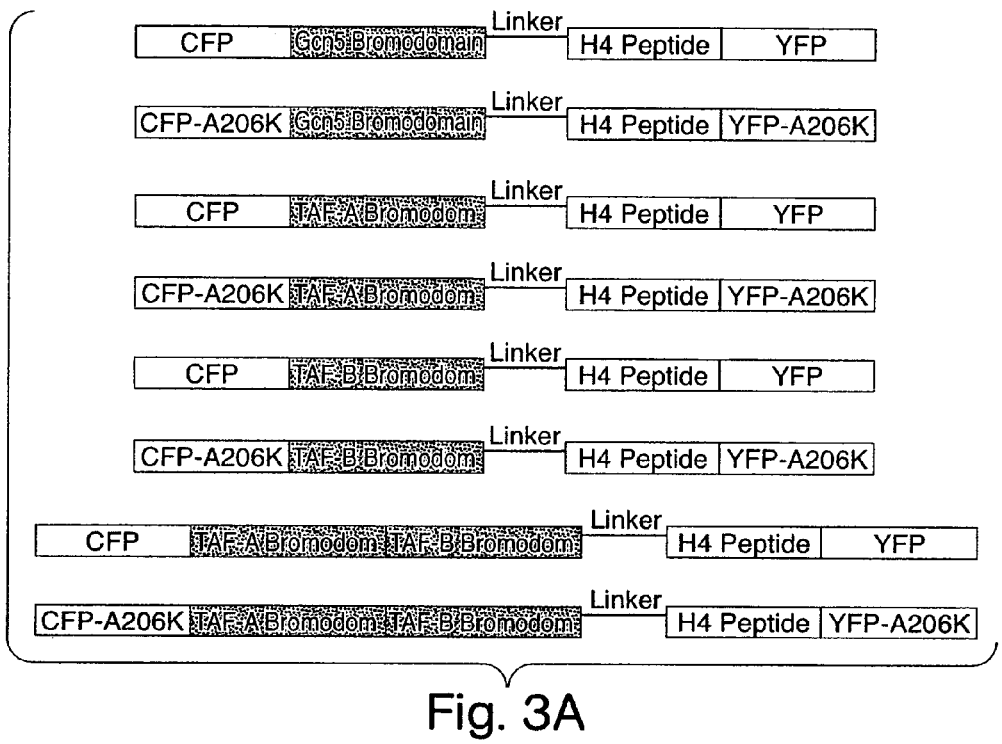
Figure 3B:
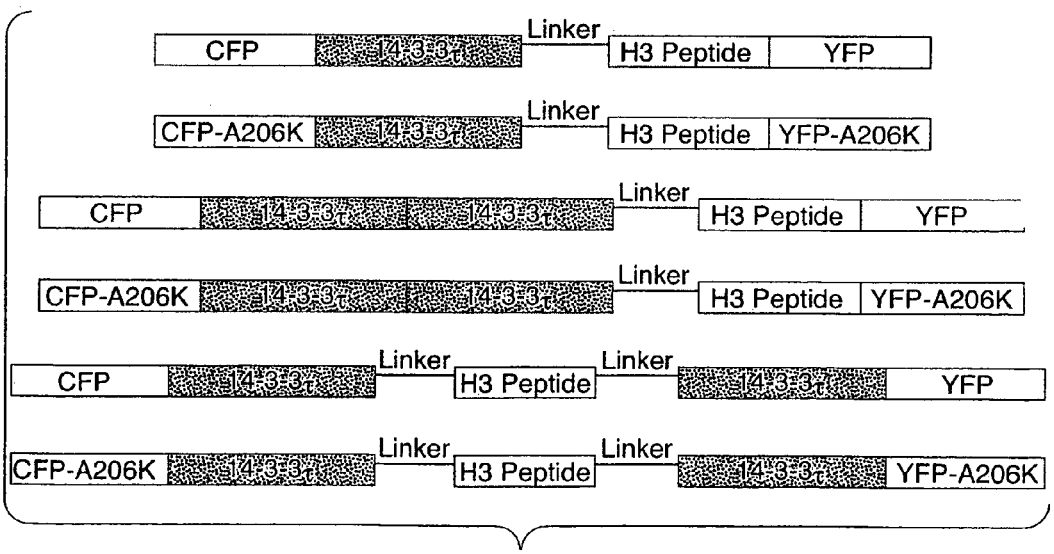

FIG. 3 shows diagrams of fusion protein reporter constructs that have been produced. FIG. 3A shows histone acetyltansferase indicator fusion protein reporters and FIG. 3B shows kinase indicator fusion protein reporters.

Figure 4A:
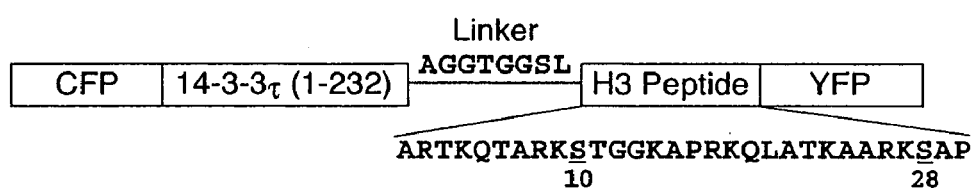
Figure 4B:
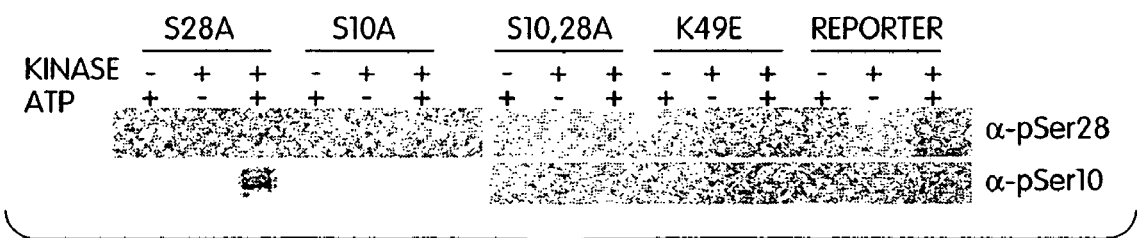

FIG. 4 shows a diagram of the domain structure of the histone 3 phosphorylation indicator (FIG. 4A). The H3 peptide segment (ARTKQTARKSTGGKAPRKQLAT-KAARKSAP; SEQ ID NO:18) of the indicator corresponds to the first 30 amino acids of the H3 protein. The known phosphorylation sites (S10 and 28) are underlined. FIG. 4B is a digitized image of Western blots depicting the phosphorylation state of the original reporter and the four point mutants after 600-minute reactions with Msk1 and ATP at 30° C. As expected, the original reporter and the K49E mutant have phosphate groups at both the S10 and S28 sites, while the other mutants lack one or both of the phosphate marks.

Figure 5:
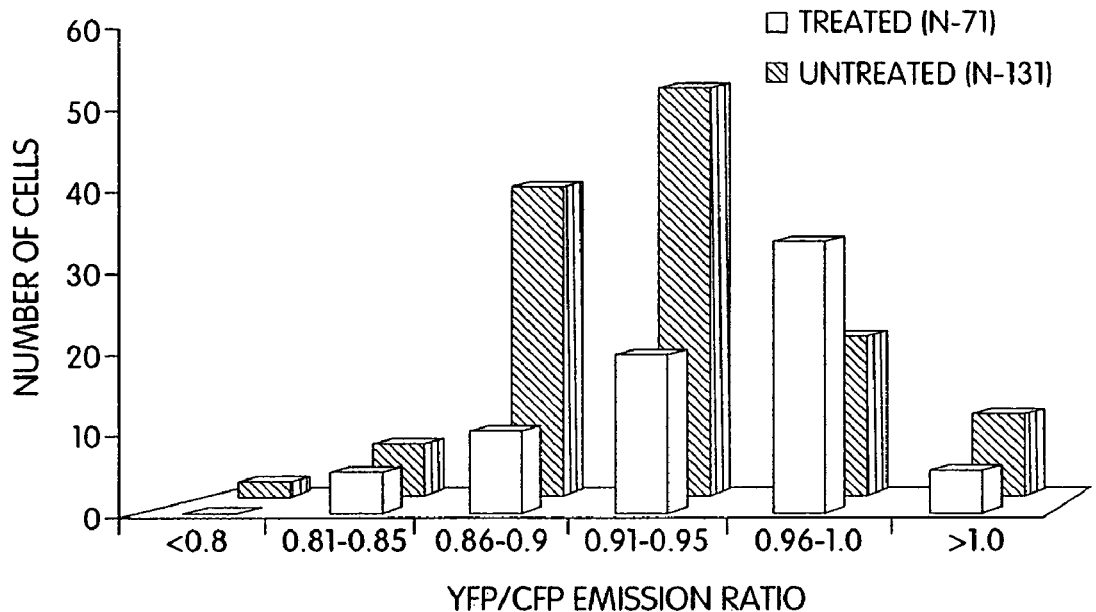

FIG. 5 is a histogram showing the distribution of YFP/CFP emission ratios for 71 nocodazole-treated cells and 131 untreated cells. Nocodazole-treated cells display, on average, higher emission ratios than untreated cells, consistent with increased H3-S28 phosphorylation levels. The experimental mean difference is 0.05, outside the 95% confidence interval for a distribution with standard deviation of 0.0511.

Figure 6:
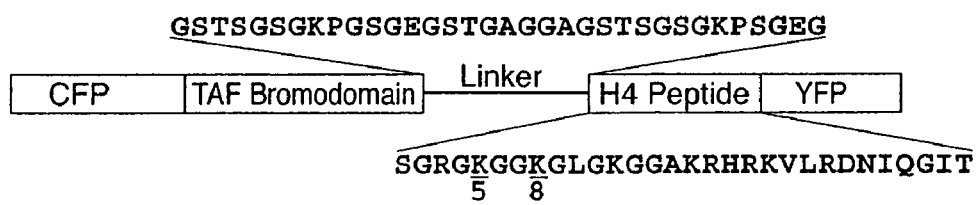

FIG. 6 is a diagram of the domain structure of the H4 acetylation indicator. The H4 peptide shown is SGRGKG-GKGLGKGGAKRHRKVLRDNIQGIT (SEQ ID NO:2).

Figure 7A:
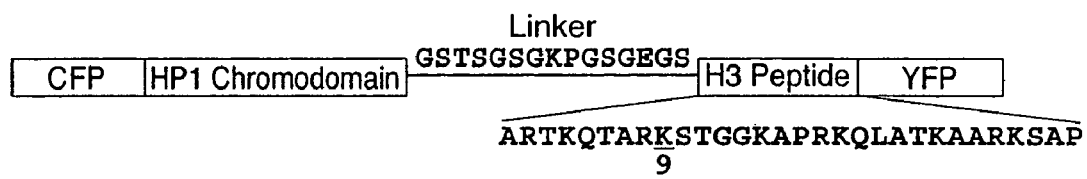
Figure 7B:
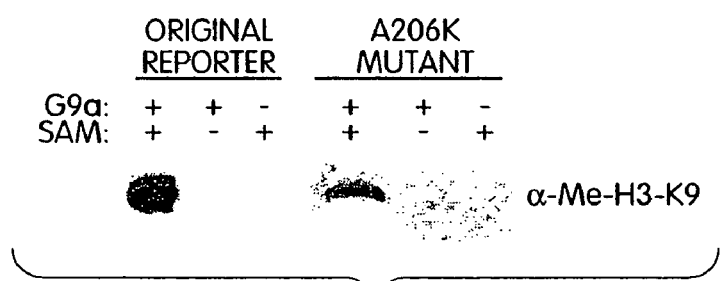

FIG. 7 shows a diagram of the domain structure of the H3 methylation indicator [FIG. 7A; ARTKQTARKSTG-GKAPRKQLATKAARKSAP (SEQ ID NO:18)]. The lysine in H3 recognized by the HP1 chromodomain is underlined. FIG. 7B is a digitized image of an immunoblot with α-methyl-H3-K9 antibody showing reporter methylation after 6 hours at 30° C. under the same reaction conditions: 3.5 µM reporter, 50 mM Tris pH 8.5, 20 mM KCl, 10 mM MgCl$_2$, 2 mM S-adenosylmethionine (SAM), 1.7 mM DTT, and an undetermined concentration of GST-tagged G9a). With either SAM or G9a left out, no methylation was observed.

DESCRIPTION OF THE SEQUENCES

SEQ ID NO:1 is an amino acid fragment of H3 ARTKQTARKSTGGKAPRKQLATKAARK-SAPATGGVKKPHR.

SEQ ID NO:2 is an amino acid fragment of H4: SGRGKGGKGLGKGGAKRHRKVLRDNIQGIT.

SEQ ID NO:3 is a bromodomain Sequence of Gnc5 is RGPHDAAIQNILTELQNHAAAWP-FLQPVNKEEVPDYYDFIKEPMDLSTMEIKL ESNKYQKMEDFIYDARLVFNNCRMYN-GENTSYYKYANRLEKFFNNKVKEIP EYSHLID SEQ ID NO:4 is the nucleotide sequence of a Gcn5-based histone acetylation fusion protein reporter.

SEQ ID NO:5 is the amino acid sequence of a Gcn5-based histone acetylation fusion protein reporter.

SEQ ID NO:6 is the nucleotide sequence of a TAFAB-based histone acetylation fusion protein reporter.

SEQ ID NO:7 is the amino acid sequence of a TAFAB-based histone acetylation fusion protein reporter.

SEQ ID NO:8 is the linker molecule: GGGGSGGGGS.

SEQ ID NO:9 is the linker molecule: GKSSGSGSESKS.

SEQ ID NO:10 is the linker molecule: GSTSGSGKS-SEGKG.

SEQ ID NO:11 is the linker molecule: GSTSGSGKSSEG-SGSTKG.

SEQ ID NO:12 is the linker molecule: GSTSGSGKS-SEGKG.

SEQ ID NO:13 is the linker molecule: GSTSGSGKPGS-GEGSTKG.

SEQ ID NO:14 is the linker molecule: EGKSSGSG-SESKEF.

SEQ ID NO:15 is the linker molecule: AGGTGGSL.

SEQ ID NO:16 is the linker molecule: GSTSGSGKPGSGEGSTGAGGAGSTSGSGKPSGEG.

SEQ ID NO: 17 is the linker molecule: GSTSGSGKPGS-GEGS.

SEQ ID NO: 18 is an amino acid fragment of H3: ARTKQTARKSTGGKAPRKQLATKAARKSAP.

SEQ ID NO:19 is the linker molecule: GGGGSGGGGSGGGGS

SEQ ID NO:20 is the linker molecule: GGGGSGGGGSGGGGSGGGGS

SEQ ID NO:21 is the linker molecule: GGGGSGGGGSGGGGSGGGGSGGGGS.

SEQ ID NO:22 is the linker molecule: GGGGSGGGGSGGGGSGGGGSGGGGSGGGGS.

DETAILED DESCRIPTION OF THE INVENTION

The invention described herein relates in part to novel fusion protein reporters and their use in the determination of levels of protein modification (e.g. histone modification) in cells. Protein (e.g. histone) modifications include, but are not limited to, acetylation, methylation and phosphorylation, and the fusion protein reporters of the invention allow the levels of such modifications to be determined in cells. It will be understood by one of ordinary skill in the art that the methods and reporters of the invention can be used to determine modification of proteins that undergo modification such as phosphorylation, methylation, and acetylation. Example of proteins for which modifications can be determined using the methods and reporters of the invention include, but are not limited to, histones, p53, and tubulin. The levels of protein modification may be compared to control levels, thus allowing a determination of whether or not a normal level of a modification is present in a cell or tissue. Levels of modification that significantly differ from levels in a control cell or tissue, are indicative of a protein modification-associated disorder. As used herein, the term "fusion protein reporter" is used interchangeably with the terms "indicator" and "reporter".

As used herein, the term, "protein modification-associated disorder" means a condition with an altered level of protein modification in a cell tissue or subject. As used herein, a protein-modification-associated disorder may include a disorder in which altered level of modification of one or more proteins. Examples of such disorders include, but are not limited to cancer, proliferative disorders, neurological disorders, muscular disorders, developmental disorders, exposure to toxins and/or toxic chemicals, viruses, and cell division and or cell development disorders, etc.

Protein modification-associated disorders also include, but are not limited to "histone modification-associated disorders", which as used herein means a condition with an altered level of histone modification in a cell, tissue, or subject. As used herein, an "altered" level means the level differs in a statistically significant way from the level in a normal or control cell, tissue, or subject. As will be understood by one of ordinary skill in the art, the level of protein modification may be an increase or a decrease of the normal or control level and be indicative of a protein modification-associated disorder. Thus, for example, an increased level of histone modification may indicate, and can be used as a marker for, a histone-modification-associated disorder and a decreased level of histone modification may indicate, and can be used as a marker for a histone-modification-associated disorder.

Histones play a role in the initial points of regulation in gene transcription. Histone modification plays a role in cell differentiation, imprinting, cell cycle progression, DNA damage/repair/recombination, chromosomal stability and disease, and thus are involved in many cell regulation functions. Histone modifications are involved in these cell processes and abnormal histone modification levels are associated with cell division and differentiation disorders. Such histone-modification-associated disorders include, but are not limited to: cancer (including but not limited to leukemia, breast cancer, ovarian cancer), exposure to toxic chemicals, viruses, developmental disorders, and cell division and or cell development disorders.

The fusion protein reporters of the invention are useful in the diagnosis of protein-modification-associated disorders, an example of which, though not intended to be limiting are histone-modification-associated disorders. In addition, the fusion protein reporters are also useful for identifying pharmaceutical agents for administration to prevent or treat protein modification-associated disorders (e.g. histone modification-associated disorders). The reporters are also useful for assessing the response of protein-modification associated disorders (e.g. histone-modification associated disorders) to treatment regimens.

As used herein, the term "fusion protein reporter" means a fusion protein that includes elements for determining the level of protein (e.g. histone) modifications in a cell. Generally, such elements include, but are not limited to, a modification-specific binding domain, a peptide that includes a polypeptide substrate sequence, and fluorescent moieties that allow detection of protein modifications. The fluorescent moieties include a donor fluorescent moiety and an acceptor fluorescent moiety positioned in the conformation of the reporter such that an alteration in the reporter conformation resulting from histone modification results in a detectable alteration in the fluorescence resonance energy transfer (FRET) between the donor and acceptor. When the conformation of the binding protein moiety changes upon substrate polypeptide (e.g. histone polypeptide) modification, the fluorescent moieties come closer together (or physically separate), and FRET is increased (or decreased) accordingly. Thus, determination of the level of FRET allows determination of the level of specific polypeptide modification of the fusion protein reporter core. As described below herein, the reporter core includes the protein-modification-specific binding domain conjugated to a polypeptide substrate. The level of protein modification in a fusion protein reporter of the invention has been determined to be substantially similar to the level of modification of endogenous proteins, thus the fusion protein reporter can be used to assess the level of endogenous protein modification in cells. For example, the level of histone modification in a fusion protein reporter of the invention has been determined to be substantially similar to the level of modification of endogenous histones, thus the fusion protein reporter can be used to assess the level of endogenous histone modification in cells.

As used herein, the term "modification-specific binding domain" means a region of a polypeptide that specifically binds to its corresponding modified polypeptide (e.g. modified histone polypeptide) but not to the unmodified form of the polypeptide. For example, an acetylation-specific binding domain specifically binds to an acetylated histone polypeptide (e.g. acetylated H3 or H4, or fragment thereof), but does not specifically bind to the unacetylated form of the histone polypeptide. Similarly, a methylation-specific binding domain specifically binds to a methylated histone polypeptide (e.g. methylated H3 or H4 or fragment thereof), but does not specifically bind to the unmethylated form of the histone polypeptide, and a phosphorylation-specific binding domain specifically binds to a phosphorylated histone polypeptide (e.g. phosphorylated H3 or H4 or fragment thereof), but does not specifically bind to the unphosphorylated form of the polypeptide.

Examples of modification-specific binding polypeptides for detecting phosphorylation modification include, but are not limited to a 14-3-3, FHA or WW domains (for 14-3-3 see Fu, H. Subramanian, R. R. & Masters, S. C. (2000) *Annu. Rev. Pharmacol. Toxicol.* 40, 617–647; Aitken, A., Jones, D., Soneji, Y. & Howell, S. (1995) *Biochem. Soc. Trans.* 23, 605–611; for FHA and WW domains see Yaffe, M. B. & Elia, A. E. *Curr. Opin. Cell Biol.* 13, 131–138 (2001)). Examples of modification-specific binding polypeptides for detecting protein acetylation (e.g. histone acetylation) include, but are not limited to, a bromodomain; and modification-specific binding polypeptides for detecting protein methylation (e.g. histone methylation), include, but are not limited to, a chromodomain. Additional modification-specific binding domains will be known to those of ordinary skill in the art as will sequence variations of the above-described modification-specific binding domains, which can also be use in the claimed invention.

As used herein, the term "bromodomain" includes, but is not limited to, bromodomains from: GCN5, P/CAF, $TAF_{II}250$, CBP, BRG1, Swi2, and Sth1. (for reviews see: *FEBS Lett* 513(1):124–8 (2002), *Front Biosci* 6:D1019–23 (2001); and *Nat Struct Biol* 6(7):601–4 (1999)). As used herein, the term "chromodomain" includes, but is not limited to: HP1, MRG15, MRG-1, cynCDY, Hrp3, dMi-2, CHD5, Swi6, and pdd3p (for review see: *Nature* 407(6802):405–9 (2000). The bromodomains and chromodomains of the invention can be from various species.

The fusion protein reporters of the invention may include a single modification-specific binding domain or may include more than one modification-specific binding domain. If more than one modification-specific binding domain is included, they may be in tandem, e.g. they may abut each other, or may be separated by other elements of the fusion protein reporter, for example, the two or more modification specific binding domains may be separated from each other by a polypeptide sequence (e.g. a histone polypeptide sequence) or a linker.

The fusion protein reporters of the invention also include a substrate polypeptide sequence. In some embodiments, the substrate polypeptide sequence is a histone polypeptide sequence. As used herein, the term "histone polypeptide sequence" means an amino acid sequence that includes all or part of a histone polypeptide amino acid sequence. The polypeptide substrate sequences of the invention may include, for instance, either complete or partial sequences of H2A, H2B, H3 and/or H4. The H3 and H4 amino acid sequences may encompass the N-terminus of the H3 or H4 polypeptides. Examples of N-terminus H3 and H4 polypeptide sequences are useful in the invention, although not intended to be limiting, are for H3: ARTKQTARKSTGGKAPRKQLATKAARKSAPATGGVKKPHR (SEQ ID NO:1), and ARTKQTARKSTGGKAPRKQLATKAARKSAP (SEQ ID NO:18) and for H4: SGRGKGGKGLGKGGAKRHRKVLRDNIQGIT (SEQ ID NO:2).

One aspect of the invention relates to the inclusion of a modification-specific binding domain and a polypeptide substrate sequence in the fusion protein reporter of the invention. In some embodiments, the polypeptide substrate sequences is a histone polypeptide sequence. As used herein, the term "core" means the modification-specific binding domain conjugated directly or indirectly with a polypeptide substrate sequence. In some embodiments, the core is a histone modification-specific binding domain conjugated directly or indirectly with a histone substrate sequence. As used herein, the term "elements" refers to the modification-specific binding domain and polypeptide substrate sequences of the core. It will be understood by one of ordinary skill in the art that in some embodiments, there is more than one modification-specific binding domain included in the core, and, as described above herein and in the Examples section, different arrangements of the core elements are embraced in embodiments of the invention. The elements of the core are conjugated to each other. As used herein, the term "conjugated," means joined or attached to each other. In some embodiments, the modification-specific binding domain is conjugated to a polypeptide substrate sequence with a linker molecule. In some embodiments, the modification-specific binding domain is conjugated to a histone polypeptide sequence with a linker molecule.

As described above, the fusion protein reporters of the invention also include donor and acceptor fluorescence protein moieties. The donor and acceptor fluorescence protein moieties may be covalently attached to the core of the fusion protein reporter. In some embodiments of the invention, determining the degree of FRET in the sample includes measuring the light emitted by the acceptor fluorescent moiety. In other embodiments of the invention, determining the degree of FRET in the sample includes measuring light emitted from the donor fluorescent moiety, measuring light emitted from the acceptor fluorescent moiety, and calculating a ratio of the light emitted from the donor fluorescent moiety and the light emitted from the acceptor fluorescent moiety. In yet other embodiments, determining the degree of FRET in the sample includes measuring the excited state lifetime of the donor moiety. The terms "donor" and "acceptor" are used broadly to encompass both traditional donors and acceptors as well as quenchers. For instance, one of the fluorescent molecules may quench light emitted by the other fluorescent molecule rather than, or in addition to, producing its own light emission.

As used herein the term "moiety" means a radical of a molecule that is attached to another radical of the fusion protein reporter. Thus a "fluorescent moiety" is the radical of a fluorescent molecule (e.g. fluorescent protein) coupled to a binding protein moiety or a linker moiety or a polypeptide substrate moiety (e.g. a histone polypeptide moiety).

In FRET, the "donor fluorescent moiety" and the "acceptor fluorescent moiety" are selected so that the donor and acceptor moieties exhibit FRET when the donor moiety is excited. One factor to be considered in choosing the donor/acceptor fluorescent moiety pair is the efficiency of FRET between the two moieties. In some embodiments, the efficiency of FRET between the donor and acceptor moieties is at least 10%, in some embodiments, at least 50%, and in other embodiments, at least 80%. The efficiency of FRET can be tested empirically using the methods described herein and known in the art.

FRET is the transfer of photonic energy between fluorophores and is a tool for characterizing molecular detail because it allows determination of changes in distance between two ends of the fusion protein reporter. The design of the fusion protein reporter, as described above, incorporates a core covalently attached to a donor fluorescent moiety at one end and an acceptor fluorescent moiety at the core's other end (including quencher pairs as described above). Thus, changes in the conformation of the core result in changes in the distance between the donor and acceptor molecules thereby resulting in alterations in FRET with modification of the core of the fusion protein reporter.

The high resolution of FRET has been used in many studies of molecular dynamics and biophysical phenomena. Additional information relating to FRET methods can be found in Forster, T. Ann. Physik 2:55–75 (1948). Tables of spectral overlap integrals are also available (for example, Berlman, I. B. Energy transfer parameters of aromatic compounds, Academic Press, New York and London (1973)). FRET is a nondestructive spectroscopic method that can monitor proximity and relative angular orientation of fluorophores in living cells and/or in real time. See, for example, Adams, S. R., et al., Nature 349:694–697 (1991), and Gonzalez, J. & Tsien, R. Y. Biophy. J. 69:1272–1280 (1995).

To undergo FRET, the emission spectrum of the donor overlaps with the excitation spectrum of the acceptor. A laser is tuned to the excitation wavelength of the donor fluorophore. The donor fluorophore emits its characteristic wavelength and with modifications such as acetylation, methylation, and/or phosphorylation of the core, the distance between the donor and acceptor changes. As the acceptor fluorophore moves into interactive proximity with the donor fluorophore, the acceptor fluorophore is excited by the energy from the donor fluorophore. The consequence of this interaction is that the emission of the donor fluorophore may be quenched and that of the acceptor fluorophore may be enhanced.

Once a fluorescence signal is generated it can then be detected and the detected signals from FRET may be analyzed in real time and/or stored in a database for analysis. The particular type of detection means will depend on the type of signal generated. Most of the interactions involved in the method will produce an electromagnetic radiation signal. Many methods are known in the art for detecting electromagnetic radiation signals. Preferred devices for detecting signals are two-dimensional imaging systems that have, among other parameters, low noise, high quantum efficiency, proper pixel-to-image correlation, and efficient processing times. An example of a device useful for detecting signals is a two-dimensional fluorescence imaging system which detects electromagnetic radiation in the fluorescent wavelength range.

There are several categories of fluorescence imaging devices based on the type of fluorescence signal measured, either intensity, lifetime, or spectra. Intensity signals can be captured by a variety of methods including charge coupled device (CCD) camera, streak cameras, and silicon diode arrays. In addition, fluorometers can be used to measure the fluorescence of samples contacted with the fusion protein reporters of the invention. Alternative imaging devices known to those of skill in the art may also be used in the methods of the invention. After the detectable signals are generated and detected the signals can be analyzed to determine protein (e.g., histone) modification information about the cell or sample.

Various factors may be balanced to optimize the efficiency and detectability of FRET from the fluorescent indicator. The emission spectrum of the donor fluorescent moiety should overlap as much as possible with the excitation spectrum of the acceptor fluorescent moiety to maximize the signal. Also, the quantum yield of the donor fluorescent moiety and the extinction coefficient of the acceptor fluorescent moiety should be as large as possible. In addition, the excitation spectra of the donor and acceptor moieties should overlap as little as possible so that a wavelength region can be found at which the donor moiety can be excited selectively and efficiently without directly exciting the acceptor moiety. In some cases, direct excitation of the acceptor moiety may be avoided because it can be difficult to distinguish direct emission from fluorescence arising from FRET. Similarly, the emission spectra of the donor and acceptor moieties should have minimal overlap so that the two emissions can be distinguished. High fluorescence quantum yield of the acceptor moiety is desirable if the emission from the acceptor moiety is to be monitored to determine the level of protein (e.g. histone) modification in a sample.

Changes in levels of protein (e.g. histone) modification concentration can be determined by monitoring FRET at a first and second time after contact between the sample and the fusion protein reporter and determining the difference in the degree of FRET. The amount of protein (e.g. histone) modification in the sample can be calculated by using a calibration curve established by titration.

The degree of FRET can be determined by any spectral or fluorescence lifetime characteristic of the excited donor moiety. For example, intensity of the fluorescent signal from the donor, the intensity of fluorescent signal from the acceptor, the ratio of the fluorescence amplitudes near the acceptor's emission maxima to the fluorescence amplitudes near the donor's emission maximum, or the excited state lifetime of the donor can be monitored.

In some embodiments, changes in the degree of FRET are determined as a function of the change in the ratio of the amount of fluorescence from the donor and acceptor moieties, a process referred to as "ratioing". Changes in the absolute amount of indicator, excitation intensity, and turbidity or other background absorbances in the sample at the excitation wavelength affect the intensities of fluorescence from both the donor and acceptor approximately in parallel. Therefore the ratio of the two emission intensities is a more robust and preferred measure of protein (e.g. histone) modification than either intensity alone.

As described above, fluorescence in a sample or cell can be measured using a fluorometer. In general, excitation radiation, from an excitation source having a first wavelength, passes through excitation optics. The excitation optics cause the excitation radiation to excite the sample. In response, fluorescent moieties in the sample emit radiation that has a wavelength that is different from the excitation wavelength. Collection optics then collect the emission from the sample or cell. The device can include a temperature controller to maintain the sample at a specific temperature while it is being scanned. According to one embodiment, a multi-axis translation stage moves a microtiter plate holding a plurality of samples or cells in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation.

Methods of performing assays on fluorescent materials are well known in the art and are described in, e.g., Lakowicz, J. R., Principles of Fluorescence Spectroscopy, New York:Plenum Press (1983); Herman, B., Resonance energy transfer microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219–243; Turro, N.J., Modern Molecular Photochemistry, Menlo Park: Benjamin/Cummings Publishing Col, Inc. (1978), pp. 296–361.

Any fluorescent moiety can be used in the invention, including proteins that fluoresce due to intramolecular rearrangements or the addition of cofactors that promote fluorescence. In the claimed invention, the change in fluorescence in the fusion protein reporter contacted with a cell is an indicator of the level of protein (e.g. histone) modification in the cell. In the claimed invention examples of fluorescent moieties are cyan fluorescent protein (CFP), enhanced cyan fluorescent protein (ECFP), yellow fluorescent protein (YFP), enhanced yellow fluorescent protein (EYFP), Citrine, Venus, and mutant forms of these fluorescent proteins. Examples of mutant forms of the proteins for use in the invention include, but are not limited to: A206K mutants (non-dimerizing) and A206D mutants. Numerous other fluorescent moieties can also be used. For example, green fluorescent proteins of cnidarians, which act as their energy-transfer acceptors in bioluminescence, are suitable fluorescent proteins for use in the fluorescent indicators. A green fluorescent protein (GFP) is a protein that emits green light, and a blue fluorescent protein (BFP) is a protein that emits blue light. GFPs have been isolated from the Pacific Northwest jellyfish, *Aequorea victoria,* the sea pansy, *Renilla reniformis,* and *Phialidium gregarium.* See, Ward, W. W., et al., Photochem. Photobiol., 35:803–808 (1982); and Levine, L. D., et al., Comp. Biochem. Physiol., 72B: 77–85 (1982).

A variety of *Aequorea*-related GFPs having useful excitation and emission spectra have been engineered by modifying the amino acid sequence of a naturally occurring GFP from *Aequorea victoria.* See, Prasher, D. C., et al., Gene, 111:229–233 (1992); Heim, R., et al., Proc. Natl. Acad. Sci., USA, 91:12501–04 (1994); U.S. Pat. No. 5,625,048, International application PCT/US95/14692, filed Nov. 10, 1995; and U.S. Pat. No. 6,124,128. The cDNA of GFP can be concatenated with those encoding many other proteins; the resulting fusions often are fluorescent and retain the biochemical features of the partner proteins. See, Cubitt, A. B., et al., Trends Biochem. Sci. 20:448–455 (1995). Mutagenesis studies have produced GFP mutants with shifted wavelengths of excitation or emission. See, Heim, R. & Tsien, R. Y. Current Biol. 6:178–182 (1996). Suitable pairs, for example a blue-shifted GFP mutant P4-3 (Y66H/Y145F) and an improved green mutant S65T can respectively serve as a donor and an acceptor for FRET. See, Tsien, R. Y., et al., Trends Cell Biol. 3:242–245 (1993). A fluorescent protein is an *Aequorea*-related fluorescent protein if any contiguous sequence of 150 amino acids of the fluorescent protein has at least 85% sequence identity with an amino acid sequence, either contiguous or non-contiguous, from the wild type *Aequorea* green fluorescent protein. In some embodiments, a fluorescent moiety is an *Aequorea*-related fluorescent protein if any contiguous sequence of 200 amino acids of the fluorescent protein has at least 95% sequence identity with an amino acid sequence, either contiguous or non-contiguous, from the wild-type *Aequorea* green fluorescent protein. Similarly, the fluorescent moiety can be related to *Renilla* or *Phialidium* wild-type fluorescent proteins using the same standards. Variants or mutants of the fluorescent proteins described herein are within the scope of the invention as described.

Other fluorescent moieties can be used in the fusion protein reporter, such as, for example, yellow fluorescent protein (YFP) from *Vibrio fischeri* strain Y-1, Peridinin-chlorophyll a binding protein from the dinoflagellate *Symbiodinium* sp. phycobiliproteins from marine cyanobacteria such as *Synechococcus,* e.g., phycoerythrin and phycocyanin, or oat phytochromes from oat reconstructed with phycoerythrobilin. These fluorescent proteins have been described in Baldwin, T. O., et al., Biochemistry 29:5509–5515 (1990), Morris, B. J., et al., Plant Molecular Biology, 24:673–677 (1994), and Wilbanks, S. M., et al., J. Biol. Chem. 268:1226–1235 (1993), and Li et al., Biochemistry 34:7923–7930 (1995).

In some embodiments, the donor fluorescent moiety is excited by ultraviolet (<400 nm) and emits blue light (<500 nm), and the acceptor fluorescent moiety is efficiently excited by blue but not by ultraviolet light and emits green light (>500 nm), for example, P4-3 and S65T, respectively. In other embodiments, the donor fluorescent moiety is excited by violet (400–430 nm) and emits blue-green (450–500 nm) and the acceptor fluorescent moiety is efficiently excited by blue-green (450–500 nm) and emits yellow-green light (520 nm), for example W1B and 10 C respectively. One of ordinary skill in the art will recognize that numerous donor and acceptor fluorescent moieties can be used in the claimed invention and will be able to determine combinations of such fluorescent moieties without undue experimentation.

The efficiency of FRET between the donor and acceptor fluorescent moieties can be adjusted by changing the ability of the two fluorescent moieties to closely associate. the nature of the protein modification-specific binding protein, polypeptide substrate, and linker molecule each affect the FRET and the response of the indicator to the protein modification. For example, the nature of the histone modification-specific binding protein, histone polypeptide and linker molecule each affect the FRET and the response of the indicator to the histone modification. Generally, large conformational changes in the binding protein moiety are desired along with a high affinity for the polypeptide substrate (e.g. the histone polypeptide).

The fusion protein reporter also includes, in some embodiments, a linker molecule that is positioned between the protein-modification specific binding protein and the polypeptide substrate in the core of the fusion protein reporter. The linker molecule attaches the protein-modification specific binding protein to the polypeptide substrate in the core and different linker molecules can be used in different aspects of the claimed invention. In some embodiments, a linker molecule that is positioned between the histone-modification specific binding protein and the histone polypeptide in the core of the fusion protein reporter. the linker molecule attaches the histone-modification specific binding protein to the histone polypeptide in the core and different linker molecules can be used in different aspects of the claimed invention. The linker moiety may be, for instance, a peptide that can include between about 1 and about 50 amino acid residues, or in some instances between about 1 amino acid residue and about 30 amino acid residues, or in some instances between 2 and about 15 residues. The linker can be a polypeptide with any amino acid sequence. In some embodiments, the linker moiety may be -Gly-Gly-.

The length of the linker molecule (described above herein) is selected to optimize both FRET and the kinetics and specificity of conformational changes induced by protein (e.g. histone) modifications. The linker molecule should be long enough and flexible enough to allow the protein-modification-specific binding protein and polypeptide substrate to freely interact and respond to protein modifications. In some embodiments, the linker molecule should be long enough and flexible enough to allow the histone-modification-specific binding protein and the histone polypeptide to freely interact and respond to histone modifications. In order to optimize the FRET effect, the average distance between the donor and acceptor fluorescent moieties should become between about 1 nm and about 10 nm, between about 1 nm and about 6 nm, or in some instances between about 1 nm and about 4 nm, when the protein (e.g. histone) modification is present (or absent). If the linker is too short or too stiff, the donor and acceptor protein moieties may not be able to readily change position. If the linker moiety is too long, the polypeptide substrate might not bind to the protein-modification-specific binding protein effectively.

The linker molecule may include flexible spacer amino acid sequences, such as those known in single-chain antibody research. For example, the linker moiety may be GGGGS (GGGGS)$_n$ (SEQ ID NO:8), GKSSGSGSESKS (SEQ ID NO:9), GSTSGSGKSSEGKG (SEQ ID NO:10), GSTSGSGKSSEGSGSTKG (SEQ ID NO:11), GSTSGSGKSSEGKG (SEQ ID NO:12), GSTSGSGKPGSGEGSTKG (SEQ ID NO:13), EGKSSGSGSESKEF (SEQ ID NO:14), AGGTGGSL (SEQ ID NO:15), GSTSGSGKPGSGEGSTGAGGAGSTSGSGKPSGEG (SEQ ID NO:16), GSTSGSGKPGSGEGS (SEQ ID NO:17), GGGGSGGGGSGGGGS (SEQ ID NO:19), GGGGSGGGGSGGGGSGGGGS (SEQ ID NO:20), GGGGSGGGGSGGGGSGGGGSGGGGS (SEQ ID NO:21), or GGGGSGGGGSGGGGSGGGGSGGGGSGGGGS (SEQ ID NO:22).

Linker molecules are described, for example, in Huston, J. S., et al., PNAS 85:5879–5883 (1988), Whitlow, M., et al., Protein Engineering 6:989–995 (1993), and Newton, D. L., et al., Biochemistry 35:545–553 (1996).

The fluorescent moieties may also include a targeting polypeptide to direct the indicator to the nucleus. A targeting polypeptide may be covalently or non-covalently attached to the fluorescent moiety. For example, a targeting polypeptide may be attached to a delivery vehicle, (e.g. a liposome), or may be directly attached to the fusion protein (e.g. covalently attached). The targeting polypeptide may be attached with or without an intervening linking molecule.

A polynucleotide encoding a target polypeptide may be ligated or fused at the 5' terminus or at the 3' terminus of a polynucleotide encoding the fluorescence protein moieties. In such an orientation the target polypeptide is located at the amino terminal end of the resulting fusion protein reporter. Examples of target polypeptides, also referred to herein as "localization sequences" include, but are not limited to, a receptor ligand, a nuclear localization sequence (NLS), a nuclear export signal (NES), a plasma membrane targeting signal, plasma membrane targeting sequences, p53, tubulin, a histone-binding protein, a histone protein, or a nuclear protein. Other targeting polypeptides with similar properties are known to those skilled in the art, or can be readily ascertained without undue experimentation.

Fragments of fusion protein reporter polypeptides can also be used in some aspects of the invention. Polypeptide fragments useful in the fusion protein reporter of the invention, preferably are those fragments that retain a distinct functional capability of the polypeptide. Functional capabilities that can be retained in a fragment of a polypeptide include the ability to interact with the other fusion protein reporter polypeptides of the invention. As will be recognized by those skilled in the art, the size of a preferred fragment will depend upon factors such as whether the fragment is of sufficient size to interact with the other fusion protein reporter polypeptides and thus enable use of the fusion protein reporter in the methods described herein. Thus, some fragments of fusion protein reporter polypeptides will consist of longer segments while others will consist of shorter segments, (e.g. 5, 6, 7, 8, 9, 10, 11, 12, 13, 14, 15, 16, 17, 18, 19, 20, 21, 22, 23, 24, 25, or more amino acids long), including each integer up to the full length of the fusion protein reporter polypeptides. An example of such full-length fusion reporter polypeptides, although not intended to be limiting are full-length H2A, H2B, H3 and/or H4 polypeptides, from any species. Examples of N-terminus H3 and H4 molecules are provided herein for H3: as SEQ ID NO:1, and SEQ ID NO:18, and for H4 as SEQ ID NO:2, and smaller fragments can be used in some embodiments, as long as the fusion protein reporter in which they are included, is functional. Such fragments may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more amino acids shorter than the full length polypeptide. It will be understood by one of ordinary skill in the art that the polypeptide may be shorter because of fewer amino acids at one end, the other end, or both ends of the polypeptide. Examples of polypeptide fragments, though not intended to be limiting include polypeptide fragments that are 1, 2, 3, 4, 5, 6, 7, 8, 9, 10, 11, 12, 13, 14, 15, 16, 17, 18, 19, 20, 21, 22, 23, 24, 25 or more amino acids shorter than SEQ ID NO:18 or SEQ ID NO:2; or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more amino acids shorter than SEQ ID NO:1. Fragments of the protein-modification-specific binding domains, (e.g. histone-modification-specific binding domain) are also contemplated. Those skilled in the art are well versed in methods for selecting functional fragments of polypeptides, which can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more amino acids shorter (at either and/or both ends) than the full length modification-specific binding domain.

The skilled artisan will also realize that conservative amino acid substitutions may be made in fusion protein reporter polypeptides (which as used herein include polypeptide substrates and/or protein-modification-specific binding domains) to provide functionally equivalent variants, or homologs of the foregoing polypeptides, i.e, the variants retain the functional capabilities of the fusion protein reporter polypeptides. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants or homologs of the fusion protein reporter polypeptides include conservative amino acid substitutions in the amino acid sequences of proteins disclosed herein. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D. For example, upon determining that a peptide is a fusion protein reporter polypeptide-equivalent polypeptide, one can make conservative amino acid substitutions to the amino acid sequence of the peptide, and the resulting fusion protein reporter polypeptide-equivalent polypeptide can be tested using methods enclosed herein to determiner whether it retain its specific binding characteristics in the fusion protein reporter.

Conservative amino-acid substitutions in the amino acid sequence of fusion protein reporter polypeptides to produce functionally equivalent variants of fusion protein reporter polypeptides typically are made by alteration of a nucleic acid encoding fusion protein reporter polypeptides. Such substitutions can be made by a variety of methods known to one of ordinary skill in the art. For example, amino acid substitutions may be made by PCR-directed mutation, site-directed mutagenesis according to the method of Kunkel (Kunkel, Proc. Nat. Acad. Sci. U.S.A. 82: 488–492, 1985), or by chemical synthesis of a gene encoding a fusion protein reporter polypeptide. Where amino acid substitutions are made to a small unique fragment of a fusion protein reporter polypeptide, the substitutions can be made by directly synthesizing the peptide. The activity of functionally equivalent fragments of fusion protein reporter polypeptides can be tested by including the altered fusion protein reporter polypeptide in a fusion protein reporter and testing for the functional capability of the fusion protein reporter polypeptide as disclosed herein. Peptides that are chemically synthesized can be tested directly for function, e.g., for activity in the fusion protein reporter.

The introduction of fusion protein reporters into cells allows those of skill in the art to monitor the level of protein (e.g. histone) modification in those cells. Additionally, use of the fusion protein reporters allows diagnosis of protein modification disorders, for example histone modification disorders as described herein. Such disorders can be identified by abnormal or aberrant levels of protein (e.g. histone) modification in cell samples. The terms "abnormal" and "aberrant" refer to either or both of a decreased level of protein (e.g. histone) modification (including no detectable protein modification) or increased level of protein (e.g. histone) modification as compared to the level of protein modification in a control sample or cell. The diagnostic methods of the invention can be used to detect the presence of a disorder associated with aberrant protein (e.g. histone) modification levels, as well as to assess the progression and/or regression of the disorder such as in response to treatment (e.g., chemotherapy, pharmaceutical, or radiation). According to this aspect of the invention, the method for diagnosing a disorder characterized by aberrant protein (e.g. histone) modification involves: detecting in a first biological sample obtained from a subject, the level of protein (e.g. histone) modification, wherein decreased level of protein modification compared to a control sample indicates that the subject has a disorder characterized by aberrant protein (e.g. histone) modification.

As used herein, a "biological sample" or "sample" includes, but is not limited to: tissue, cells, or body fluid (e.g., blood). A fluid sample may include cells and fluid. The tissue and cells may be obtained from a subject or may be grown in culture (e.g. from a cell line). The tissue or cells may be obtained (e.g., from a tissue biopsy, aspiration, or fluid collection) using methods well known to those of ordinary skill in the related medical arts. As used herein the term "subject" means a mammal, including humans, non-human primates, dogs, cats, horses, pigs, cattle, sheep, and rodents, including but not limited to mice and rats.

The phrase "suspected of having a protein modification disorder" as used herein means a tissue or tissue sample that may contain cells with abnormal (either increased or decreased) levels of protein modification. As used herein, the phrase "suspected of having a histone modification disorder" means a tissue or tissue sample that may contain cells with abnormal (either increased or decreased) levels of histone modification. Examples of methods for obtaining the sample from the biopsy include aspiration, gross apportioning of a mass, microdissection, laser-based microdissection, or other art-known cell-separation methods. As used herein, the terms "increase," "decrease," and "difference" preferably mean significant increase, decrease, and difference respectively, e.g. statistically significant.

It will be understood by one of ordinary skill in the art that some disorders will exhibit an increase in protein (e.g. histone) modifications relative to those in normal cells and tissues and other disorders will exhibit a decrease in protein (e.g. histone) modifications relative to those in normal cells. Because the fusion protein reporter of the claimed invention can detect either an increase or decrease in the level of protein (e.g. histone) modification in cells and tissues it can be used to determining the existence of either category of disorder.

There may be reduced levels of protein (e.g. histone) modification in cells and tissues in some disorders. In these cells and tissues, a determination of the level of protein (e.g. histone) modification is diagnostic of a protein-modification-associated disorder if the level of protein modification is below a baseline level determined for that tissue or cell type. The baseline level of protein modification can be determined using controls known to those of skill in the art. Such methods include, for example, assaying a number of histologically normal tissue samples from subjects that are clinically normal (i.e., do not have clinical signs of a protein-modification-associated disorder in the tissue type) and determining the mean level of protein modification for the samples. This baseline level can then be compared to the level protein modification in other samples and cells and can serve as a control baseline level for diagnostic comparisons.

The determination that the level of protein (e.g. histone) modification is above a baseline level determined for that tissue or cell type, alternatively, may indicate the presence of a protein-modification-associated disorder, e.g. a histone-modification-associated disorder, in the cell or tissue.

Thus, in some cells and tissues there is a baseline level of protein modification that can be assessed using the fusion protein reporter of the invention, and it is that baseline/control level that determines the level below which a level of protein modification indicates a protein-modification-associated disorder in the tissue. Therefore, in these disorders, the level of protein modification indicates a protein-modification-associated disorder in the tissue when the level of protein modification is less than about 95% of that in a control tissue sample. A level of protein modification of less than about 99%, 95%, 90%, 80%, 70%, 60%, 50%, 40%, 30%, 20%, 10%, 5%, or less of the level of protein modification in the control tissue indicates a protein-modification-associated disorder in the tissue. Thus, a level of histone modification of less than about 99%, 95%, 90%, 80%, 70%, 60%, 50%, 40%, 30%, 20%, 10%, 5%, or less of the level of histone modification in the control tissue indicates a histone-modification-associated disorder in the tissue.

A baseline level of protein (e.g. histone) modification can also be used in the assessment of disorders that are associated with an increase in protein modification. In such disorders, an increase in the level of protein modification in a sample cell, relative to the baseline/control level, indicates the presence of the disorder in the cell. In these disorders, the level of protein modification indicates a protein-modification-associated disorder in the tissue when the level of protein modification is more than about 105% of that in a control tissue sample. A level of protein modification of more than about 110%, 115%, 120%, 125%, 130%, 135%, 140%, 150, 160% 170% or more than the level of protein modification in the control tissue indicates a protein-modification-associated disorder in the tissue. Thus, a level of histone modification of more than about 110%, 115%, 120%, 125%, 130%, 135%, 140%, 150, 160% 170% or more than the level of histone modification in the control tissue indicates a histone-modification-associated disorder in the tissue.

As used herein the term "control" means predetermined values, and also means baseline controls. Examples include samples from control populations or control samples generated through manufacture to baseline controls for experimental samples.

As used herein the term "control" includes positive and negative controls which may be a predetermined value that can take a variety of forms. The control(s) can be a single cut-off value, such as a median or mean, or can be established based upon comparative groups, such as in groups having normal levels of protein (e.g. histone) modification in cells and tissues and groups having abnormal levels of protein (e.g. histone) modification in cells and tissues. Another example of a comparative group is a group having a particular disease, condition and/or symptoms and a group without the disease, condition and/or symptoms. Another comparative group is a group with a family history of a particular disease and a group without such a family history of the particular disease. The predetermined control value can be arranged, for example, where a tested population is divided equally (or unequally) into groups, such as a low-risk group, a medium-risk group and a high-risk group or into quadrants or quintiles, the lowest quadrant or quintile being individuals with the lowest risk or highest protein (e.g. histone) modification levels in a disorder indicated by decreased protein (e.g. histone) modification. Similarly, the highest quadrant or quintile being individuals with the highest risk or lowest protein (e.g. histone) modification levels in a disorder indicated by decreased protein (e.g. histone) modification. It will be understood that in a disorder characterized by increased protein (e.g histone) modification, the lowest quadrant or quintile will include individuals with the lowest risk or lowest protein (e.g. histone) modification levels and the highest quadrant or quintile will include individuals with the highest risk or highest protein (e.g. histone) modification levels.

The predetermined value of a control will depend upon the particular population selected. For example, an apparently healthy population (or cells or subjects) will have a different "normal" protein (e.g. histone) modification level range than will a population which is known to have a condition characterized by aberrant levels of protein (e.g. histone) modification. Accordingly, the predetermined value selected may take into account the category in which an individual falls. Appropriate ranges and categories can be selected with no more than routine experimentation by those of ordinary skill in the art. Typically the control will be based on apparently healthy individuals in an appropriate age bracket. By "decrease" it is meant less protein (e.g. histone) modification relative to a selected control. By "increase" it is meant more protein (e.g. histone) modification relative to a selected control.

The invention also includes methods to monitor the onset, progression, or regression of protein-modification-asociated disorders in a subject by, for example, obtaining cell or tissue samples at sequential times from a subject and assaying such samples for the level of protein modification using the fusion protein reporter of the invention. A subject may be suspected of having a protein-modification-asociated disorder or may be believed not to have a protein-modification-asociated disorder and the sample can serve as a baseline level for comparison with subsequent cell or tissue samples from the subject.

Onset of a condition is the initiation of the physiological changes or characteristics associated with the condition in a subject. Such changes may be evidenced by physiological symptoms, or may be clinically asymptomatic. For example, the onset of a protein-modification-associated disorder (e.g. a histone-modification-associated disorder) may be followed by a period during which there may be protein-modification-associated disorder physiological characteristics in the subject, even though clinical symptoms may not be evident at that time. The progression of a condition follows onset and is the advancement of the physiological characteristics of the condition, which may or may not be marked by an increase in clinical symptoms. In contrast, the regression of a condition is a decrease in physiological characteristics of the condition, perhaps with a parallel reduction in symptoms, and may result from a treatment or may be a natural reversal in the condition.

The level of protein-modification in a cell or tissue sample from a subject that is determined to be at a level below (or in some disorders a level above) the baseline level for that protein modification, is an indicator for a protein-modification-associated disorder in the subject. For example, in a type of a histone-modification-associated disorder in which a level of histone modification is known to be decreased, the determination that the level of the histone modification in a cell or tissue sample is below the level in a normal control tissue, would be diagnostic for the histone-modification-associated disorder. A similar method can be used to determine the presence of a histone-modification-associated disorder in which an increase in the level of histone modification is indicative of the disorder. The level of protein (e.g. histone) modification may be determined by measuring the fluorescence level following contacting the cell with the fusion protein reporter of the invention.

The onset of a protein-modification-associated disorder may be indicated by the increase or decrease in the level of histone modification in a sample from a subject as compared to the level of protein modification determined in a previous sample from the subject. Thus, if the level of histone modification is determined to be lower or higher in a second sample from a subject when compared to the level determined in a first sample from a subject, this is an indication of the onset of a histone-modification-associated disorder in the subject.

Progression and regression of a protein modification-associated disorder may be indicated by the alteration of the level of protein modification a subject's samples over time. An example of which, though not intending to be limiting is that in disorders characterized by decreased levels of histone modification, progression of a histone-modification-associated disorder is indicated when there is a decrease in the level of histone modification in cells obtained from a subject as compared to the level in cells previously obtained from the same subject. Similarly, regression of such histone-modification-associated disorders may be indicated when there is determined to be an increase in the level of histone modification in cells obtained from a subject as compared to the level in cells previously obtained from the same subject. The methods and reporters of the invention are also useful for assessing progression and/or regression in other protein modification-associated disorders.

One of ordinary skill in the art will recognize that for a disorder characterized by an increase in protein modification, progression of the disorder may be indicated when there is a statistical increase in the level of protein modification in a cell sample, relative to the level of the protein modification determined in a previous cell sample. Similarly, regression of such a protein-modification-associated disorder may be indicated when the level of protein modification determined in cells obtained from a subject, is statistically less than the level determined in cells previously obtained from the subject.

The invention also includes kits that include the fusion protein reporter of the invention. An example of a kit of the invention is a kit that provides components necessary to determine the level of protein (e.g. histone) modification in a cell or tissue sample. Components in such kits may include a fusion protein reporter of the invention and instructions for its use to assess protein (e.g. histone) modification levels. The kits of the invention can include instructions or other printed material on how to use the various components of the kits for diagnostic purposes. Additional materials may be included in any or all kits of the invention, and such materials may include, but are not limited to buffers, water, enzymes, tubes, control molecules, etc.

The invention further provides efficient methods of identifying pharmacological agents or lead compounds for pharmaceutical agents that either enhance or inhibit protein (e.g. histone) modification. Generally, the screening methods involve use of the fusion protein reporter to assay for compounds that modulate (i.e increase or decrease) protein (e.g. histone) modification levels.

Typically, a plurality of fusion protein reporter assays are run in parallel with different pharmaceutical compound concentrations to obtain a different response to the various concentrations. Typically, one of these concentrations serves as a negative control, i.e., at zero concentration of the pharmaceutical or at a concentration of the pharmaceutical compound below the limits of assay detection. Candidate agents encompass numerous chemical classes, although typically they are organic compounds. Preferably, the candidate pharmacological agents are small organic compounds, i.e., those having a molecular weight of more than 50 and less than about 2500, preferably less than about 1000 and, more preferably, less than about 500. Candidate agents comprise functional chemical groups necessary for structural interactions with proteins and/or nucleic acid molecules, and typically include at least an amine, carbonyl, hydroxyl or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like. Where the agent is a nucleic acid molecule, the agent typically is a DNA or RNA molecule, although modified nucleic acid molecules are also contemplated.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily be modified through conventional chemical, physical, and biochemical means. Further, known pharmacological agents may be subjected to directed or random chemical modifications such as acylation, alkylation, esterification, amidification, etc. to produce structural analogs of the agents.

A variety of other reagents also can be included in the mixture. These include reagents such as salts, buffers, neutral proteins (e.g., albumin), detergents, etc., which may be used to facilitate optimal activity of the assay. Such a reagent may also reduce non-specific or background interactions of the reaction components. Other reagents that improve the efficiency of the assay such as protease inhibitors, nuclease inhibitors, antimicrobial agents, and the like may also be used.

An exemplary histone modification assay is described herein using the fusion protein reporter. Modification assays of the invention are also useful to assess modification of other proteins that undergo methylation and acetylation. In general, the mixture of the foregoing assay materials, including a fusion protein reporter, is incubated under conditions whereby, but for the presence of the candidate pharmacological agent, the level of fluorescence remains similar or equal to that of a control assay. The order of addition of components, incubation temperature, time of incubation, and other parameters of the assay may be readily determined. Such experimentation merely involves optimization of the assay parameters, not the fundamental composition of the assay. After incubation, the level of histone modification can be detected by any convenient method available to the user.

Yet another aspect of the invention relates to use of the methods and reporters of the invention in in vitro and in vivo assays of pharmacological agents that alter protein (e.g. histone) modification in a sample (e.g. cells, tissues etc) or in a subject. The methods of the invention relate, in part, to the assessment of the action and/or effect of candidate pharmacological agents on protein (e.g. histone) modification in cells, tissues, and/or subjects In some aspects of the invention, protein modification reporters of the invention can be used to assess protein (e.g. histone) modification in vitro, e.g. in cells that are contacted with a candidate pharmacological agent and the protein (e.g. histone) modification in contacted cells and/or tissues can be compared to control levels of protein (e.g. histone) modification, e.g. in cells and/or tissues not contacted with the candidate pharmacological agent. In some embodiments, the assay of the effect of a candidate pharmacological agent in vivo can be tested using the methods and reporters of the invention. For example, a biological sample can be obtained from a subject and tested for protein (e.g. histone) modification using a reporter of the invention and a candidate pharmacological agent can then be administered to the subject and a subsequent biological sample can be taken from the subject and assayed for protein (e.g. histone) modification using the methods and reporters of the invention. The results of the assays at different timepoints (e.g., before and after administration of the pharmaceutical agent) can be compared as a measure of the effect of the pharmacological agent on protein (e.g. histone) modification in the subject. The methods and reporters of the invention are also useful to determine an effective amount of a pharmacological agent useful for treating a protein-modification-associated disorder, for example a histone-modification-associated disorder.

The candidate pharmaceutical agents and compositions used in the foregoing methods preferably are sterile and contain an effective amount of a pharmacological agent for producing the desired response in a unit of weight or volume suitable for administration to a patient. The doses of pharmacological agents administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits. The dosage of a pharmacological agent of the invention may be adjusted by the individual physician or veterinarian, particularly in the event of any complication. A therapeutically effective amount typically varies from 0.01 mg/kg to about 1000 mg/kg, preferably from about 0.1 mg/kg to about 200 mg/kg, and most preferably from about 0.2 mg/kg to about 20 mg/kg, in one or more dose administrations daily, for one or more days.

Various modes of administration will be known to one of ordinary skill in the art which effectively deliver the pharmacological agents of the invention to a desired tissue, cell, or bodily fluid. The administration methods include: topical, intravenous, oral, inhalation, intracavity, intrathecal, intrasynovial, buccal, sublingual, intranasal, transdermal, intravitreal, subcutaneous, intramuscular and intradermal administration. The invention is not limited by the particular modes of administration disclosed herein. Standard references in the art (e.g., *Remington's Pharmaceutical Sciences,* 20th Edition, Lippincott, Williams and Wilkins, Baltimore Md., 2001) provide modes of administration and formulations for delivery of various pharmaceutical preparations and formulations in pharmaceutical carriers. Other protocols which are useful for the administration of pharmacological agents of the invention will be known to one of ordinary skill in the art, in which the dose amount, schedule of administration, sites of administration, mode of administration (e.g., intra-organ) and the like vary from those presented herein.

Administration of pharmacological agents of the invention to mammals other than humans, e.g. for testing purposes or veterinary therapeutic purposes, is carried out under substantially the same conditions as described above. It will be understood by one of ordinary skill in the art that this invention is applicable to both human and animal diseases including protein-modification-associated diseases of the invention. Thus, this invention is intended to be used in husbandry and veterinary medicine as well as in human therapeutics.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. Preferred components of the composition are described above in conjunction with the description of the pharmacological agents and/or compositions of the invention.

A pharmacological agent or composition may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the pharmacological agents of the invention, and with each other, in a manner such that there is no interaction which would substantially impair the desired pharmaceutical efficacy.

The pharmaceutical compositions may contain suitable buffering agents, as described above, including: acetate, phosphate, citrate, glycine, borate, carbonate, bicarbonate, hydroxide (and other bases) and pharmaceutically acceptable salts of the foregoing compounds. The pharmaceutical compositions also may contain, optionally, suitable preservatives, such as: benzalkonium chloride; chlorobutanol; parabens and thimerosal.

The pharmaceutical compositions may conveniently be presented in unit dosage form and may be prepared by any of the methods well known in the art of pharmacy. All methods include the step of bringing the active agent into association with a carrier, which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions suitable for parenteral administration may be formulated according to known methods using suitable dispersing or wetting agents and suspending agents. The sterile injectable preparation also may be a sterile injectable solution or suspension in a non-toxic parenterally acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid may be used in the preparation of injectables. Carrier formulation suitable for oral, subcutaneous, intravenous, intramuscular, etc. administrations can be found in *Remington's Pharmaceutical Sciences,* Mack Publishing Co., Easton, Pa.

The invention also relates in some aspects to methods for detecting environmental agents. Cells respond to chemical or biological agents in their environment with extremely high specificity and sensitivity. Cell responses may include protein (e.g. histone) modifications that can be determined by the methods and/or fusion protein reporters of the invention. Thus, wild-type or engineered cells equipped with fluorescent readout can be incorporated into biodevices for rapid detection of such agents, for instance, in battlefield and homeland defense settings. In addition, the fusion protein reporters of the invention can be used to facilitate medical diagnosis following military or civilian personnel exposure to biological agents, thus promoting rapid staging of infection status, which is critical to treatment decisions. Various stages of viral infection, for example, are reflected by changes in cellular state. These changes can be monitored by expressed fluorescence indicators to provide rapid diagnosis and triage. These techniques can also be used in an enlistment setting to detect occult clinical conditions in prospective enlistees.

An additional aspect of the invention involves characterization of risk susceptibility in subjects. The response to chemical and biological insult varies not only by agent but also by tissue type and by subject. Because the fusion protein reporters of the invention can be general and easily expressed in cells, they will enable whole-cell, multiple-tissue testing of individual subjects for susceptibility to biological or chemical agents likely to be encountered in a particular combat theater. This testing would be a holistic complement to the reductionist, sequence-based approach of pharmacogenomics.

The invention also relates in part to the construction of expression vectors and the expression of genes in transfected cells involves the use of molecular cloning techniques also well known in the art. Sambrook et al., Molecular Cloning—A Laboratory Manual, Cold Spring Harbor Laboratory, Cold Spring Harbor, N.Y., (1989) and Current Protocols in Molecular Biology, F. M. Ausubel et al., eds., (Current Protocols, a joint venture between Greene Publishing Associates, Inc. and John Wiley & Sons, Inc., most recent Supplement).

In some aspects of the invention, an expression vector comprising any of the isolated nucleic acid molecules of the invention, preferably operably linked to a promoter. In a related aspect, host cells transformed or transfected with such expression vectors also are provided.

The invention provides various research methods and compositions. Thus, according to one aspect of the invention, a method for producing the fusion protein reporter is provided. The method involves providing a sequence that encodes the core and flanking fluorescent protein moieties operably linked to a promoter; expressing the fusion protein reporter in an expression system; and isolating the fusion protein reporter from the expression system.

As used herein, a "vector" may be any of a number of nucleic acid molecules into which a desired sequence may be inserted by restriction and ligation for transport between different genetic environments or for expression in a host cell. Vectors are typically composed of DNA although RNA vectors are also available. Vectors include, but are not limited to, plasmids, phagemids, and virus genomes. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art, e.g., β-galactosidase or alkaline phosphatase, and genes which visibly affect the phenotype of transformed or transfected cells, hosts, colonies or plaques. Preferred vectors are those capable of autonomous replication and expression of the structural gene products present in the DNA segments to which they are operably joined.

As used herein, a coding sequence and regulatory sequences are said to be "operably joined" when they are covalently linked in such a way as to place the expression or transcription of the coding sequence under the influence or control of the regulatory sequences. As used herein, "operably joined" and "operably linked" are used interchangeably and should be construed to have the same meaning. In embodiments of the invention in which it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Often, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

It will also be recognized that the invention embraces the use of the fusion protein reporter DNA and genomic sequences in expression vectors, as well as to transfect host cells and cell lines, be these prokaryotic, e.g., E. coli, or eukaryotic, e.g., CHO cells, COS cells, yeast expression systems, and recombinant baculovirus expression in insect cells. Especially useful are mammalian cells such as human, mouse, hamster, pig, goat, primate, etc. They may be of a wide variety of tissue types, including mast cells, fibroblasts, oocytes, and lymphocytes, and may be primary cells and cell lines. Specific examples include dendritic cells, U293 cells keratinocytes, peripheral blood leukocytes, bone marrow stem cells and embryonic stem cells. The expression vectors require that the pertinent sequence, i.e., those nucleic acids described supra, be operably linked to a promoter.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA or RNA encoding the fusion protein reporter, or fragments, or variants thereof. The heterologous DNA or RNA is placed under operable control of transcriptional elements to permit the expression of the heterologous DNA in the host cell.

Preferred systems for mRNA expression in mammalian cells are those such as pcDNA1.1 and pCDM8 (Invitrogen) that contain a selectable marker (which facilitates the selection of stably transfected cell lines) and contain the human cytomegalovirus (CMV) enhancer-promoter sequences, Additionally, suitable for expression in primate or canine cell lines is the pCEP4 vector (Invitrogen), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mizushima and Nagata (*Nuc. Acids Res.* 18:5322, 1990), and its use in transfection experiments is disclosed by, for example, Demoulin (*Mol. Cell. Biol.* 16:4710–4716, 1996). Still another preferred expression vector is an adenovirus, described by Stratford-Perricaudet, which is defective for E1 and E3 proteins (*J. Clin. Invest.* 90:626–630, 1992). The use of the adenovirus as an Adeno. P1A recombinant is described by Wamier et al., in intradermal injection in mice for immunization against P1A (*Int. J. Cancer*, 67:303–310, 1996).

The invention also embraces kits termed expression kits, which allow the artisan to prepare a desired expression vector or vectors. Such expression kits include at least separate portions of each of the previously discussed coding sequences. Other components may be added, as desired, as long as the previously mentioned sequences are included.

Fusion protein reporters of the invention can be can also be expressed recombinantly in a variety of prokaryotic and eukaryotic expression systems by constructing an expression vector appropriate to the expression system, introducing the expression vector into the expression system, and isolating the recombinantly expressed protein.

Thus, as used herein with respect to proteins, "isolated" means separated from its native environment and present in sufficient quantity to permit its identification or use. Isolated, when referring to a protein or polypeptide, means, for example: (i) selectively produced by expression of a recombinant nucleic acid or (ii) purified as by chromatography or electrophoresis. Isolated proteins or polypeptides may, but need not be, substantially pure. The term "substantially pure" means that the proteins or polypeptides are essentially free of other substances with which they may be found in nature or in vivo systems to an extent practical and appropriate for their intended use. Substantially pure proteins may be produced by techniques well known in the art. Because an isolated protein may be admixed with a pharmaceutically acceptable carrier in a pharmaceutical preparation, the protein may comprise only a small percentage by weight of the preparation. The protein is nonetheless isolated in that it has been separated from the substances with which it may be associated in living systems, e.g., isolated from other proteins.

It will be understood by one of ordinary skill in the art that variants of the polypeptides that comprise the fusion protein reporter, or fluorophore carrying proteins, of the invention, and variations of the nucleic acids that encode these polypeptides, are also contemplated in some aspects of the invention. As used herein, the term "fusion protein reporter polypeptide" means a polypeptide sequence that forms part of the core of the fusion protein reporter. Variants of the polypeptides can include homologs. A homolog of a fusion protein reporter polypeptide is a polypeptide from a human or other animal that has a high degree of structural similarity to an identified fusion protein reporter polypeptide of the invention, e.g., at least about 75%, 80%, 85%, 90%, 95% or more amino acid sequence identity. Identification of human and other organism homologs of fusion protein reporter polypeptides will be familiar to those of skill in the art. In general, nucleic acid hybridization is a suitable method for identification of homologous sequences of another species (e.g., human, cow, sheep), that correspond to a known sequence. Standard nucleic acid hybridization procedures can be used to identify related nucleic acid sequences of selected percent identity. For example, one can construct a library of cDNAs reverse transcribed from the mRNA of a selected tissue and use the nucleic acids that encode fusion protein reporter polypeptides identified herein to screen the library for related nucleotide sequences. The screening preferably is performed using high-stringency conditions to identify those sequences that are closely related by sequence identity. Nucleic acids so identified can be translated into polypeptides and incorporated into fusion protein reporters which can be tested for functional ability to detect protein (e.g. histone) modification using the assay as described herein.

The terms "high stringency" and "highly stringent" as used herein refer to parameters with which the art is familiar. Nucleic acid hybridization parameters may be found in references that compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, high-stringency conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$(pH7), 0.5% SDS, 2 mM EDTA). SSC is 0.15M sodium chloride/0.015M sodium citrate, pH7; SDS is sodium dodecyl sulphate; and EDTA is ethylenediaminetetracetic acid. After hybridization, the membrane upon which the DNA is transferred is washed, for example, in 2×SSC at room temperature and then at 0.1–0.5×SSC/0.1×SDS at temperatures up to 68° C.

There are other conditions, reagents, and so forth that can be used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of nucleic acids that encode fusion protein reporter polypeptides of the invention (e.g., by using lower stringency conditions). The skilled artisan also is familiar with the methodology for screening cells and libraries for expression of such molecules, which then are routinely isolated, followed by isolation of the pertinent nucleic acid molecule and sequencing.

In general, fusion protein reporter homologs and alleles typically will share at least 90% nucleotide identity and/or at least 95% amino acid identity to the sequences of fusion protein reporter polypeptides or fragments thereof, and precursors thereof, nucleic acid and polypeptides, respectively, in some instances will share at least 95% nucleotide identity and/or at least 97% amino acid identity, and in other instances will share at least 97% nucleotide identity and/or at least 99% amino acid identity. The homology can be calculated using various, publicly available software tools developed by NCBI (Bethesda, Md.) that can be obtained through the Internet. Exemplary tools include the BLAST system available from the website of the National Center for Biotechnology Information (NCBI) at the National Institutes of Health. Pairwise and ClustalW alignments (BLOSUM30 matrix setting) as well as Kyte-Doolittle hydropathic analysis can be obtained using the MacVector sequence analysis software (Oxford Molecular Group).

Identification of related sequences can also be achieved using conventional methods known to those of ordinary skill in the art, for example, the polymerase chain reaction (PCR) and other amplification techniques suitable for cloning related nucleic acid sequences. Preferably, PCR primers are selected to amplify portions of a nucleic acid sequence believed to be conserved (e.g., a binding domain, etc.). Again, nucleic acids are preferably amplified from a tissue-specific library.

The invention also includes degenerate nucleic acids that include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating fusion protein reporter polypeptide. Similarly, nucleotide sequence triplets which encode other amino acid residues include, but are not limited to: CCA, CCC, CCG, and CCT (proline codons); CGA, CGC, CGG, CGT, AGA, and AGG (arginine codons); ACA, ACC, ACG, and ACT (threonine codons); AAC and AAT (asparagine codons); and ATA, ATC, and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides modified nucleic acid molecules, which include additions, substitutions and deletions of one or more nucleotides (preferably 1–20 nucleotides) that are useful for practicing the invention. As used herein the terms: "deletion," "addition," and "substitution," mean deletion, addition, and substitution changes to 1, 2, 3, 4, 5, 6, 7,8,9, 10, 11, 12, 13, 14, 15 ,16, 17, 18, 19, 20, 21, 22, 23, 24, 25, 26, 27, 28, 29, 30, or more nucleic acids of a sequence of the invention. In preferred embodiments, these modified nucleic acid molecules and/or the polypeptides they encode retain at least one activity or function of the unmodified nucleic acid molecule and/or the polypeptides disclosed herein, such as binding, etc. In certain embodiments, the modified nucleic acid molecules encode modified polypeptides, preferably polypeptides having conservative amino acid substitutions as are described elsewhere herein.

The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

For example, modified nucleic acid molecules that encode polypeptides having single amino acid changes can be prepared. Each of these nucleic acid molecules can have one, two, or three nucleotide substitutions exclusive of nucleotide changes corresponding to the degeneracy of the genetic code as described herein. Likewise, modified nucleic acid molecules that encode polypeptides having two amino acid changes can be prepared which have, e.g., 2–6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s)) also can be prepared and are embraced by the invention as readily envisioned by one of ordinary skill in the art. Any of the foregoing nucleic acids or polypeptides can be tested by routine experimentation for retention of structural relation or activity to the nucleic acids and/or polypeptides disclosed herein.

EXAMPLES

Example 1

Three Classes of Noninvasive Cell-State Indicators with Simple, Real-Time Optical Readout.

Introduction

Indicators for kinases, acetyltransferases, and methyltransferases have been developed. Such indicators are also referred to herein as fusion protein reporters. In the design of the fusion protein reporter (FIG. 2A), a peptide substrate was fused to a phosphopeptide-specific binding protein and the pair was sandwiched between a FRET-capable pair of FPs (CFP and YFP). Phosphorylation of the peptide substrate by a kinase causes intramolecular complexation between the phosphopeptide and the binding domain, leading to a change in distance between the CFP and YFP and therefore resulting in a change in FRET. High specificity can be programmed into this indicator by tuning the substrate sequence or by fusing the indicator to localization domains, and the overall design is highly modular and generalizable. In addition, reporter sensitivity is high. The technology is also minimally invasive, since it perturbs no native protein expression levels, and can easily be introduced by transfection. As used herein the terms indicator and indicators are used interchangeably with the terms fusion protein reporter and fusion protein reporters, respectively.

Histone Modifying-Enzyme Activity Reporters

Figure 1:
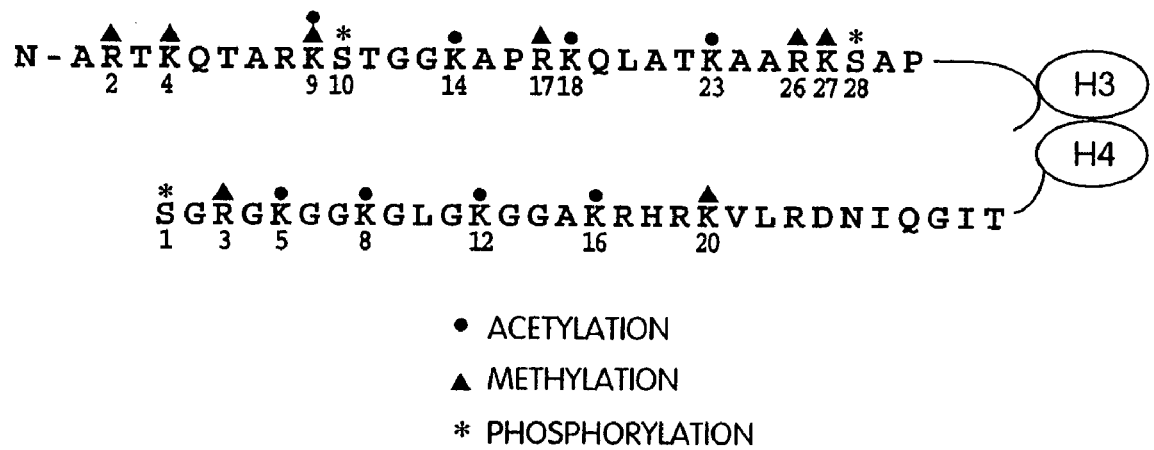
FIG. 1 is a diagram that shows the sites of post-translational modification on H3 and H4 tails. (●=acetylation, ▲=methylation, and *=phosphorylation. (Adapted from Zhang, Y. and Reinberg, D. Genes and Dev. 15:2343–2360, (2001)).

Histone proteins, which provide scaffolding support for DNA in the nuclei of all eukaryotic cells, can be covalently modified in various ways to influence the transcription levels of the proximal DNA. The core nucleosome particle is a histone octamer consisting of two copies each of H2A, H2B, H3 and H4, wrapped inside 146 base pairs of DNA. Covalent modifications to the N-terminal tails of H3 and H4, such as phosphorylation, acetylation, methylation, ubiquitination, or ADP-ribosylation, give rise to structural changes and create binding sites for signaling proteins that regulate transcription (FIG. 1). The first three of these modifications, performed respectively by kinases, acetyltransferases, and methyltransferases, have well-established roles in the regulation of chromatin status and hence of gene transcription; we have taken the following approach to develop reporters for each of these modifications. We have built reporters by fusing, in order from N- to C-terminus, cyan fluorescent protein (CFP), a binding domain specific for the modified histone sequence of interest, a peptide substrate corresponding to the N-terminus of H3 or H4, and yellow fluorescent protein (YFP) (FIGS. 2A and 2B). Modification of the peptide substrate by a kinase, acetyltransferase, or methyltransferase then allows it to form an intramolecular complex with the binding domain, increasing FRET between the two flanking fluorescent moieties. Removal of the modification by a phosphatase, deacetylase, or (if methylation is reversible) demethylase reverses the FRET change. This design is optimized empirically to maximize responsivity by interchanging the donor and acceptor or the substrate and binding domain, or by varying the length and content of interdomain spacer sequences (linker sequences).

These indicators report the activation state of histone-modifying enzymes by mimicking full-length endogenous histones and acting as surrogate substrates for kinases, acetyltransferases, or methyltransferases in the nucleus. The rate and specificity of enzymatic modification of the indicator reflect the modification of the endogenous histones, providing a real-time readout. Because each enzyme can modify many reporter molecules, thereby amplifying the signal, the reporter is highly sensitive. Two features of the reporter contribute to high spatial resolution. First, the reporter is a large (~75 kD) protein, limiting its rate of diffusion in the nucleus and allowing visualization of local enzymatic activity as a local change in FRET. Second, the reporter construct itself can be targeted to subcellular compartments such as the nucleus, chromatin in general, or heterochromatin in particular by genetic fusion to a targeting polypeptide, such as a nuclear localization sequence (NLS), histone proteins, or the heterochromatin-associated protein HP1, respectively. A reporter thus tethered will report the modification state of the histone to which it is attached.

The modification-specific binding domain used in each indicator varies according to the enzyme class under study. To construct indicators for the detection of acetyltransferase activity, natural acetyl-lysine binding domains known as bromodomains are used. Kinetic and structural studies have shown that this conserved ~110-amino-acid module found in many nuclear signaling proteins binds selectively to acetylated lysines. For example, the bromodomain of the P/CAF histone acetyltransferase binds with a $K_d$ of 346 μM to an acetylated peptide corresponding to the N-terminus of H4, but not to the unacetylated peptide (Dhalluin, C. et al., Nature, 1999, 399, 491–496). Similarly, the two tandem bromodomains of the transcription factor subunit $TAF_{II}250$ bind with a $K_d$ of 1 μM to the diacetylated peptide corresponding to the N-terminus of H4, to the monoacetylated peptide with a $K_d$ of 40 μM, and not at all to the unacetylated peptide (Jacobson, R. H. et al., Science, 2000, 288, 1422–1425).

Either of these bromodomains is fused to an H4 substrate peptide and sandwiched between CFP and YFP to create indicators of H4 acetylation. The relatively weak affinity of the single bromodomain for acetylated peptides beneficially causes it to favor intramolecular complexation with the neighboring substrate over intermolecular complexation with endogenous acetylated histones. Furthermore, if the bromodomain is kinetically similar to the SH2 phosphotyrosine binding domain, the complex "breathes," allowing HDACs to gain steric access to and deacetylate the substrate, reversing the FRET increase.

Analogous reporters for kinase and methyltransferase activities are produced by replacing the bromodomain with a methylation- or phosphorylation-specific binding domain. Many such domains exist in Nature. For detection of phosphorylated serine side chains in H3 and H4 tails, natural phosphoserine/threonine-binding domains such as 14-3-3, FHA, or WW are used. For the construction of methyltransferase reporters, the chromodomain is a likely methyl-lysine-specific binding domain (Marmorstein, R., Nat. Rev. Mol. Cell Biol., 2001, 2, 422–432). Because no histone demethylase has yet been found, our fusion protein reporter should help determine whether histone methylation is reversible, assist in the search for a histone demethylase (if one exists), and help elucidate the biological role of histone methylation.

Methods and Results

Preparation of Fusion Protein Reporters

A panel of kinase and acetyltransferase indicators with the structures shown in FIG. 3 was prepared. In addition to using conventional CFP and YFP in the construction of the indicators, engineered versions were also produced using the newly discovered CFP-A206K and YFP-A206K mutants (Zacharias, D.A. et al., Science, 2002, 296(5569);913–916). These mutants have identical spectroscopic properties to the FPs from which they were derived, but the single point mutation eliminates the weak tendency of the parent proteins to dimerize. This substitution therefore generated indicators with different conformational properties and improve responsivity to the enzymes they were designed to detect. The indicators shown in FIG. 3 were expressed in E. coli with N-terminal hexahistidine tags to aid purification, and are tested with both commercial and self-prepared enzymes in vitro.

Testing the Fusion Protein Reporters

For the kinase indicators, the histone kinases Msk-1, Rsk-2, Ipl-1, Aurora A&B, and NIMA are tested. Msk-1 and Rsk-2 have been purchased from Upstate Biotechnology (Waltham, Mass.); the remaining enzymes are expressed and purified in-house from the bacterial expression constructs generously provided to us by the labs of David Allis, Stephan Osmani, and Paolo Sassone-Corsi. The acetyltransferase indicators are tested using the commercially-available enzyme PCAF, as well as Gcn5, MOF, and CBP. Changes in FRET are monitored in a cuvette over time as the purified indicators are incubated with the appropriate enzymes. As, suitable responses to phosphorylation, acetylation, and methylation are obtained, the indicators, fused to a nuclear localization sequence, are transfected into mammalian cells.

Characterization of the cellular FRET response to strong global modifiers of enzyme activation state, such as enzyme and protein synthesis inhibitors, or inducible enzyme overexpression, and testing of appropriate indicator and signaling-enzyme mutants as mechanism-specific positive and negative controls verify the properties of the indicators. One potential complication is that multi-site modification of the substrate sequences may interfere with binding to the modification-specific domains. In such cases, the interfering sites are removed by site-directed mutagenesis. For example, to study heterochromatin duplication, a reporter for H4 acetylation will need only lysines 5 and 12 intact, as these correspond to the acetylation sites for newly synthesized histones.

Example 2

Methods

Library-Based Reporter Development and Optimization

The above strategies result in development and optimization of a wide variety of fusion proteins incorporating fluorescent moieties, enzyme substrates, and modification-specific binding domains. Although successful chimeras are found by designing and expressing constructs one by one, it is faster and more efficient to devise high-throughput strategies for systematically generating and testing diverse libraries of such constructs. Libraries of reporter mutants are therefore screened by both in vitro and in vivo methods. For in vitro screening, the DNA libraries are transformed into *E. coli* and grown on antibiotic plates. Using an automated colony-picker, fluorescent clones (indicating that CFP and YFP are present and properly folded) are selected and transferred into 96-well plates containing growth media. A protein expression robot, available at the Whitehead Institute, Cambridge, Mass., is used to culture the bacteria in 96-well plates, lyse them, and purify the proteins with Ni-NTA agarose beads. The robot is capable of generating pure protein from $10^5$ different cultures in 48 hours. The robot's growth and purification conditions are adapted to our GFP constructs. Existing chimeras are used, such as the $Ca^{+2}$ responsive cameleons, as positive controls in the initial testing and optimization. Arrays of chimeric proteins are obtained, and are assayed with a microplate fluorometer by comparing the emission of the acceptor YFP before and after addition of purified enzyme. Because the donor and acceptor GFPs of our indicator are part of the same chimera, ratios of the two emissions reflect only FRET rather than variable protein concentrations in each well. Constructs with a large response are mapped back to their original bacterial sample, and the encoding DNA is extracted.

For in vivo screening, our libraries are transfected into a standard mammalian culture line such as HeLa, CHO, HEK-293, 3T3, or Jurkat. To ensure monocopy transfection, a retroviral infection method is used. Library sizes are $10^5$–$10^6$. Fluorescence-activated cell sorting (FACS) is used to screen for mutants with the best responsivity in three separate passes. First, nonfluorescent cells are discarded. Second, cells with high acceptor emission in the absence of a particular external stimulus are discarded. Third, cells with low acceptor emission in the presence of that stimulus are discarded. These selections reduce the cell pool to a size assayable by fluorescence microscopy; the change in ratio of acceptor to donor emission with stimulation is the final selection criterion. Based on our experience with other chimeras, expression levels of our reporter in mammalian cells is more than adequate for FACS. Incubation times are based on radiolabeling experiments in permeabilized cells.

When pools of mutants with enhanced responsivity are obtained by the in vitro and in vivo screens, they are used as templates for the preparation of second-generation libraries. By repeating the screens with increasingly stringent fluorescence emission cut-offs, the reporters are optimized. The constructs are characterized in detail for specificity, kinetics, and potential fluorescence artifacts.

Example 3

Use of Fusion Protein Reporters to Study the Mechanism of Heterochromatin Duplication during Mammalian Cell Division.

Epigenetic Inheritance of Histone Modification Patterns

Introduction

One process in chromatin research that remains almost entirely opaque is that of epigenetic pattern duplication during cell division. It is known that genes that are silent in a parent cell often remain silent in the daughter cells after cell division. On a larger scale, entire heterochromatin domains (chromosomal regions that remain intensely stained throughout the cell cycle and contain large numbers of silenced genes) and euchromatin domains ("open" chromatin containing more actively expressed genes) are preserved during the process of cell division. What is the molecular mechanism for the accurate duplication of these epigenetic patterns? Unlike DNA, for which there is a natural base complement system to form the basis of a replication mechanism, epigenetic modifications such as acetylation and methylation do not appear to have such a code. The mechanism of histone modification pattern duplication is especially unclear, in comparison to DNA methylation pattern duplication, which is believed to be mediated by DNA methyltransferases, which recognize and bind to hemi-methylated DNA to generate symmetric fully-methylated DNA.

Role of FP-Based Indicators in the Study of Histone Modification Pattern Duplication The fusion protein reporters of the invention help facilitate the study of epigenetic pattern duplication during cell division. Histone modification states are currently detected and analyzed by immunofluorescence staining or chromatin immunoprecipitation (ChIP). In the former, fixed cells are stained by antibodies specific for histone bearing particular modifications. The latter technique involves sequential cell lysis, chromatin isolation based on modification state, and DNA analysis by PCR. Because these methods are both perturbative and involve discontinuous data collection and, for ChIP, averaging over large populations of cells, they tend to compromise spatial and/or temporal resolution. The development of reporters which can dynamically probe the activities of histone-modifying enzymes as a function of chromatin functional environment (high DNA methylation or histone acetylation levels, for example) or cell cycle phase helps clarify the molecular mechanism of epigenetic inheritance.

Methods

The fusion protein reporters of the invention are used to study the heterochromatin duplication process by monitoring the rate and extent of H4 deacetylation as a function of chromatin functional environment (spatial readout) and cell cycle phase (temporal readout). For example, to test the hypothesis that histone deacetylases (HDACs) are specifically targeted to heterochromatin domains through association with heterochromatin-specific proteins, the modification probes are fused to HP1, CAF-1, a methyl-DNA-binding protein (such as the MDB domain of MeCP2), or a chromodomain. Changes in the rate or magnitude of the FRET response in comparison to untargeted probe supports roles for the fusion partners in directing HDAC activity during heterochromatin duplication. The effect of chromatin functional environment on H4 deacetylation are probed by looking for patterns of HDAC activity in relation to replication fork clusters. The hypothesis that DNA replication complexes induce the local recruitment and/or activation of HDACs at replication forks predicts that the lowest FRET signals, corresponding to the lowest degree of reporter acetylation, coincide with replication fork clusters. To visualize replication fork clusters simultaneously in living cells with reporter FRET signals, mRFP- (Campbell, R. E. et al., *Proc Natl Acad Sci USA*, 2002, 99(12)7877–82) fused HP1 are co-expressed. HP1 is a general marker for heterochromatin, but it is known to concentrate at replication forks clusters (replication forks are visualized as especially bright dots by HP1 immunofluorescence staining) (Taddei, A. et al., *J Cell Biol.*, 1999, 147, 1153–1166). Therefore low levels of mRFP-HP1 are expressed and replication fork sites are followed in living cells.

Increases or decreases in reporter FRET as a function of cell cycle phase are also revealing. If HDAC activity is controlled by DNA replication machinery, reporter FRET must reach a minimum sometime during S phase. If, on the other hand, HDAC activity is constitutively associated with heterochromatin domains, it should be possible to detect deacetylation of the reporter in the vicinity of heterochromatin throughout the entire cell cycle. Together, these experiments provide a continuous view of dynamic histone modifications in particular chromatin functional environments throughout the cell cycle, helping to differentiate between the various models of heterochromatin duplication.

Example 4

Use of Fusion Protein Reporters to Detect Chemical and Biological Warfare (CBW) Agents in the Environment and to Detect Other Environmental Agents.

Introduction

Many cellular responses to toxins, physical stresses, and inflammatory cytokines occur via signaling through the stress-activated protein kinase (SAPK) and/or the p38 family kinases. Stimuli capable of activating these kinases include ultraviolet light, oxidative stress (such as singlet oxygen), nitric oxide, sodium arsenite, methyl-methane sulphonate (MMS), the protein synthesis inhibitors anisomycin and cycloheximide, and the cytotoxic anticancer agents Ara-C, cisplatinum, mitomycin C, taxol, adriamycin, vinblastine, etoposide, teniposide, and dexamethasone. Once activated, both SAPK and p38 alter gene expression levels, which result in outcomes such as apoptosis, immune activation, inflammation, or adaptation to environmental changes. Because these two kinases are part of common downstream pathways responding to a variety of environmental insults, they represent an opportunity to engineer first-line screening biodevices, which would report the presence of a wide range of toxic agents.

Methods

Customized fluorescent indicators are used in two ways to capitalize on these inherent cellular mechanisms. First, specific indicators for one of the two key intermediate kinases, SAPK or p38, are constructed by dialing in a substrate sequence that matches the specificity of one or both of these kinases. The fluorescent indicators so generated change color on activation of these kinases by environmental insults. Indicator specificity is further increased by fusing these indicators through a flexible linker to SAPK or p38 themselves. Second, both the SAPK and p38 kinase pathways converge even further downstream by activating histone H3 kinases. A reporter incorporating the H3 N-terminal tail sequence and a 14-3-3 domain for specific phosphoserine recognition is capable of detecting either SAPK- or p38-induced H3 phosphorylation.

These fusion protein reporters (indicators), which can be included in biodevices for detection uses, including, but not limited to battlefield use, differ from the fusion protein reporters described above herein. First, the indicators are expressed in hardy organisms, such as yeast, which express the eukaryotic SAPK/p38 stress pathway but can survive in a minimally regulated environment. Second, the transgenic organism as a whole is optimized by a combination of rational design and library-based screening to optimize responsivity to environmental agents and/or to develop specificity for a single toxin of interest. Third, the transgenic organism is incorporated into a small, robust device together with a detector that can measure the donor/acceptor fluorescence intensity ratio easily and accurately.

Example 5

A Histone Phosphorylation Reporter

We constructed an indicator for phosphorylation of histone 3 (H3) by incorporating the 14-3-3τ domain as the phosphoserine recognition element, and the N-terminal segment of H3 as the modification sequence (FIG. 4A). FIG. 4A shows the domain structure of the histone 3 phosphorylation indicator. The H3 peptide segment of the indicator corresponds to the first 30 amino acids of the H3 protein. The known phosphorylation sites (S10 and 28) are underlined in FIG. 4A. The protease-resistant linker sequence is expected to reach from the C-terminus of 14-3-3τ to the phosphoserine binding pocket, based on the 14-3-3τ crystal structure (Yaffe, M.B. et al, 1997, *Cell* 91, 961–971.). 14-3-3τ was selected because although no binding partners for phosphorylated H3 had been reported in the literature, peptide panning experiments by Yaffe et al. suggested that 14-3-3τ might have the correct specificity to bind phosphorylated H3 (Yaffe, M. B. et al, 2001, *Nat. Biotechnol.* 19, 348–353.).

The reporter was overexpressed in *E. coli* and purified by nickel affinity chromatography. On in vitro phosphorylation by the purified H3 kinase Msk-1, (New,L. et al,1999, *J. Biol. Chem.* 274, 1026–1032.) the reporter responded with a 25% emission ratio increase (YFP/CFP). The emission spectra showed the response of the reporter to in vitro phosphorylation by Msk1. Over 340 minutes at 30° C., the YFP/CFP emission ratio of the indicator increased by 25% (reaction conditions: 2 μM reporter, 0.6 mM ATP, 20 mM Hepes pH 7.7, 10 mM MgCl$_2$, 0.1 mM EGTA, 0.5 mM DTT, and an undetermined concentration of His$_6$Msk-1). Leaving out the ATP abolished the FRET change. The spectrum of the reporter after digestion with trypsin was also determined. Since CFP and YFP are trypsin-resistant, the disappearance of the YFP peak at 530 nm was consistent with intramolecular as opposed to intermolecular FRET. The FRET increase required both ATP and Msk-1.

Analysis of several site-directed mutants demonstrated that both the phosphorylation site and the 14-3-3τ domain needed to be intact for the reporter to give a FRET response, consistent with an intramolecular complexation mechanism. Time courses were determined that showed the YFP/CFP emission ratio change of the original reporter and four point mutants [(1) Ser10→Ala, (2) Ser10→Ala;Ser28→Ala, (3) Lys49→Glu and (4) Ser28→Ala]. Elimination of the 14-3-3τ binding affinity (K49E) abolished the FRET change. The two serine phosphorylation sites were non-equivalent: the S10A mutant still gave a FRET change comparable to that of the original reporter, while the S28A mutant (and the S10A/S28A double mutant) lost its responsivity. The results indicate that the reporter is specific for detection of phosphorylation at the H3-S28 site.

Interestingly, although Msk-1 phosphorylated both serine 10 (S10) and serine 28 (S28) of the H3 peptide sequence (FIG. 4B), only phosphorylation at S28 gave a FRET response, while phosphorylation at S10 alone had no effect. FIG. 4B shows Western blots depicting the phosphorylation state of the original reporter and the four point mutants after 600-minute reactions with Msk1 and ATP at 30° C. As expected, the original reporter and the K49E mutant had phosphate groups at both the S10 and S28 sites, while the other mutants lacked one or both of the phosphate marks. The results suggested that either 14-3-3τ had no affinity for phosphorylated S10, or the design of the reporter sterically restricted intramolecular binding between the S10 site and the 14-3-3τ domain. The reporter appeared to specifically report on H3-S28 phosphorylation in vitro.

Because S28 phosphorylation is a known mitotic marker, (Goto, H. et al,1999, *J. Biol. Chem.* 274, 25543–25549.) the reporter was tested in HeLa cells to see if a FRET increase could be detected during cell division. Cells were transfected with a plasmid containing the reporter gene fused to a nuclear localization signal (NLS), and 12–18 hours later, nocodazole, a reversible inhibitor of microtubule polymerization, was added to arrest cells in M phase (the reported peak of S28 phosphorylation). HeLa cells transfected with the reporter were treated with the microtubule polymerization inhibitor nocodazole (0.75 μg/mL) for 16 hours. The treated cells showed a rounded morphology typical for cells arrested in M phase. Cells treated with nocodazole display higher levels of FRET, consistent with an increased level of H3-S28 phosphorylation. We then removed the nocodazole by replacing the culture medium and allowing the cells to recover for 11 hours and then determining the YFP/CFP emission ratio. As expected, the cells progressed through the remainder of the cell cycle, flattened out, and displayed lower FRET levels. The histogram in FIG. 5 shows the distribution of YFP/CFP emission ratios in cells treated with nocodazole compared to untreated cells (N=202). FIG. 5 shows the distribution of emission ratios for 71 nocodazole-treated cells and 131 untreated cells. Nocodazole-treated cells displayed, on average, higher emission ratios than untreated cells, consistent with increased H3-S28 phosphorylation levels. The experimental mean difference was 0.05, outside the 95% confidence interval for a distribution with standard deviation of 0.0511. As expected, the nocodazole-treated cells displayed higher emission ratios, consistent with an increase in the level of H3-S28 phosphorylation. We are testing the reporter in single cells in a continuous imaging mode to determine whether reporter FRET has the expected periodic pattern coincident with the cell cycle.

Example 6

A Histone Acetylation Reporter

We also successfully constructed a reporter for histone acetylation, the first for this particular class of post-translational modification (FIG. 6). For the recognition element, we used the bromodomain of the *Drosophila* transcription factor TAF$_{250}$. Tjian et al. have reported that this bromodomain specifically binds to acetylated lysines in the N-terminal region of histone 4 (H4) (Jacobson, R. H. et al., 2000, *Science* 288, 1422–1425.). The domain structure of our histone acetylation reporter is shown in FIG. 6. When treated with the histone acetyltransferase enzyme CBP (Perissi,V. et a.l, 1999, *Proc. Natl. Acad. Sci. U.S.A.* 3652–3657.) in the presence of acetyl-CoA, an 11% increase in YFP/CFP emission ratio was observed. The emission spectra show the response of the reporter to in vitro acetylation by CBP histone acetyltransferase at 30° C. The reaction conditions for the experiment were: 0.5 μM reporter, 4.1 mM acetyl-CoA, 50 mM Tris pH 7.4, 100 mM NaCl, and an undetermined concentration of GST-tagged CBP. We assessed the FRET change in four conditions: (1)+Acetyl-CoA+CBP, (2)+Acetyl-CoA, (3)+CBP, and (4) Reporter only. We determined that the FRET change required both enzyme and acetyl-CoA. We assessed the YFP/CFP emission ratio change of the reporter in an acetylation reactions over time. Leaving out the CBP or acetyl-CoA eliminated the FRET response.

Site-directed mutagenesis studies are performed to verify that the FRET response results from the interaction between bromodomain and acetylated substrate peptide. The reporter is tested in vivo using trichostatin A, a non-specific inhibitor of histone deacetylases, which should cause a global increase in the level of histone acetylation, inducing a FRET increase.

Example 7

A Histone Methylation Reporter

We designed and constructed a histone methylation reporter using the chromodomain of HP1 as the methyl-lysine recognition domain (Nielsen, P. R. et al., 2002, *Nature* 416, 103–107.) and the first 30 amino acids of H3 as the substrate domain (FIG. 7A). FIG. 7A shows the domain structure of the H3 methylation indicator. The lysine in H3 recognized by the HP1 chromodomain is underlined. On methylation by recombinant G9a histone methyltransferase in vitro, (Tachibana, M. et al,2002, *Genes Dev.* 16, 1779–1791.) the reporter gives a 20% emission ratio increase. We determined the emission spectra showing the response of the reporter to in vitro methylation by G9a methyltransferase at 30° C. In the experiment the reaction conditions were: 3.5 μM reporter, 50 mM Tris pH 8.5, 20 mM KCl, 10 mM MgCl$_2$, 2 mM S-adenosylmethionine (SAM), 1.7 mM DTT, and an undetermined concentration of GST-tagged G9a). Four reactions were assessed: (1) G9a+SAM (A206K mutant), (2) G9a+SAM, (3) G9a only, and (4) SAM only. FIG. 7B shows an immunoblot with α-methyl-H3-K9 antibody showing reporter methylation after 6 hours at 30° C. under the same reaction conditions above. With either SAM or G9a left out, no methylation was observed.

The FRET response was eliminated when either the enzyme or its cofactor, S-adenosylmethionine, was omitted. We determined the YFP/CFP emission ratio change of the reporter in a methylation reaction over a 35000 second time course. Leaving out the G9a or SAM eliminated the FRET response. The non-dimerizing A206K mutant gave the same FRET response as the original reporter. Similar FRET levels and responsivity were seen in a reporter mutant in which both the CFP and YFP domains bear the A206K mutation. This mutation is known to eliminate the weak tendency of the fluorescent proteins to dimerize; (Zacharias, D. A. et al, 2002, *Science* 296, 913–916.) therefore, dimerization of our original reporter is unlikely to play a role in the FRET change.

Based on the known specificity of G9a for methylation at H3-K9, (Tachibana, M. et al., 2002, *Genes Dev.* 16, 1779–1791.) and the known affinity of the HP1 chromodomain for binding to methylated H3-K9, (Nielsen, P. R. et al., 2002, *Nature* 416, 103–107.) we surmise that our reporter is responding to H3-K9 methylation. However, we are using site-directed mutagenesis to confirm this, and to test specificity using other histone methyltransferases. We are developing other methylation reporters with different chromodomains (such as the polycomb chromodomain) to recognize other lysine methylation sites in H3 and H4.

Example 8

Reporters of Protein Phosphorylation

We have developed a reporter for H3-S28 phosphorylation (see previous examples). For additional in vitro characterization of this reporter, we: (1) determine how well the indicator reflects the kinetics of endogenous H3 phosphorylation by Msk-1 via a comparative kinetic study, (2) determine whether the reporter dimerizes through its 14-3-3τ domain, and (3) check the FRET response to a non-specific phosphatase such as PP1 (FRET decrease is expected).

A reporter is also constructed for the other major phosphorylation site on H3, serine 10 (S10) (Fischle, W. et al., 2003, *Cell Biol.* 15, 172–183.). Phosphorylation at S10 appears to be involved in the mediation of both immediate-early response gene transcription (Cheung, P. et al., 2000, *Mol. Cell* 5, 905–915.) and stress-induced apoptosis (Zhong, S. et al., 2001, *J. Biol. Chem.* 276, 33213–33219.). To develop a reporter for this position, we replace 14-3-3τ with other phosphoserine binding domains. At the same time, we are varying the sequence of the existing H3-S28 phosphorylation reporter to overcome its lack of response to S10 phosphorylation. By truncating the 14-3-3τ portion to suppress possible dimerization (Fu, H. et al., 2000, *Annu. Rev. Pharmacol. Toxicol.* 40, 617–647.) or extending the linker to relieve possible steric constraints, the reporter may become sensitive to S10 phosphorylation. In an S28/S10-responsive reporter obtained by this approach, the substrate S28 residue is mutated to alanine to obtain an S10-specific reporter. The two serines are sufficiently distant that mutation should not affect reporter interaction with endogenous H3 kinases.

Demonstration that the Protein Phosphorylation Reporters Work in the Live Cell Context.

We have shown that our H3-S28 phosphorylation reporter detects an increase in S28 phosphorylation in HeLa cells arrested in M phase by nocodazole (See Example 5). To confirm these results we correlate the FRET change to reporter phosphorylation state, measured independently by Western blot. We also perform a number of genetic and pharmacological controls. For instance, the FRET change should be abolished if the S28A mutant is substituted for native reporter, or if cells are pre-treated with H89, a small-molecule inhibitor of Msk-1 (Zhong, S. et al., 2001, *J. Biol. Chem.* 276, 33213–33219.). To complement our FRET histogram, we also perform continuous imaging of single cells, expecting to observe a periodic FRET pattern coincident with the cell cycle.

To enhance the spatial resolution of our cellular measurements, we are also tethering the reporter to H3 itself. This tethering immobilizes the reporter within chromatin, eliminating diffusion and enabling imaging of H3 phosphorylation in dividing cells with very high spatial resolution. An H3-GFP fusion construct has already been used by Cook et al. (Kimura, H. et al.) to measure the kinetics of core histone exchange in cells. The C-terminal GFP tag does not inhibit the incorporation of H3 into chromatin or affect the modification of the N-terminal tail by kinases or acetyltransferases. We are generating an analogous H3-reporter fusion and introducing it into HeLa cells by transient transfection. The larger size of our reporter tag (~2.5 times the size of GFP) is not expected to be problematic, but we compare the properties of the H3-reporter fusion to endogenous H3 by several criteria: (1) acetylation, phosphorylation, and methylation (detected by immunoblotting), (2) fraction of soluble (unincorporated) protein (by NaCl extraction), (3) protease sensitivities, and (4) localization pattern (by immunofluorescence staining).

If fusion of the reporter to H3 is tolerated, it is possible to image H3-S28 phosphorylation in cells at very high spatial resolution. Each tagged H3 molecule is phosphorylated at two sites: within the fused full H3 domain, and within the H3 substrate motif of the reporter molecule. Because of their close spatial proximity, the phosphorylation state of the reporter H3 motif should mirror that of the fused H3 domain. Because the chromatin environment is sterically congested, the reporter might not fold to give the intramolecular complex as readily as it does in solution. We therefore need to fully characterize the H3-fused reporter with the panel of experiments and associated controls described above for the untargeted reporter. If reporter responsivity is compromised by fusion to H3, we extend the linker length and investigate attachment to the N- rather than C-terminal end of H3.

Development of a phosphorylation reporter for S10, the other serine site in H3, is followed by testing in mouse 10 T1/2 cells stimulated by epidermal growth factor (EGF). Allis et al. have reported a transient (onset after 15 min, duration 30–60 min) increase in H3-S10 phosphorylation levels on addition of EGF to serum-starved cells (Cheung, P. et al., 2000, *Mol. Cell* 5, 905–915.).

Example 9

Reporters of Protein Acetylation

Our first reporter for H4 acetylation has been developed and gives an 11% emission ratio change on in vitro acetylation (see Examples above). Characterization studies of this reporter include: (1) construction of mutant control reporters to check that the FRET response results, as designed, from intramolecular binding of bromodomain to acetylated substrate sequence, (2) determination of the acetylation site(s) responsible for the FRET change (most likely natural CBP acetyltransferase substrate sites K5 and/or K8), (3) confirmation by Western blot that reporter FRET correlates with reporter acetylation state, (4) comparative kinetic studies of reporter vs. native H4, and (5) investigation of reporter response to purified histone deacetylase enzymes.

As with the phosphorylation reporters, a panel of acetylation reporters specific for each of the known acetylation sites on histones 3 and 4 is developed. Through an iterative process of gross engineering and targeted mutagenesis, a 'toolbox' of useful acetylation reporters is created for studying epigenetic inheritance.

Demonstration that the Protein Acetylation Reporters Work in the Live Cell Context.

Cellular characterization of the H4 acetylation reporter is examined. The reporter is introduced into HeLa cells by transient transfection, and the cells are treated with trichostatin A, a non-specific histone deacetylase (HDAC) inhibitor. If HDACs are inhibited, the overall level of acetylation in the nucleus rises and an increase in reporter FRET is observed.

If this initial experiment is successful, we proceed to full cellular characterization. The in vitro data suggest that our H4 acetylation reporter is responsive to modification at the K5 and K8 residues of H4, known substrate sites for recombinant CBP. Several interventions are known to induce K5 and/or K8 acetylation in vivo. Some of these act via activation of p300/CBP, such as treatment of MCF-7 cells with estrogen or retinoic acid (onset ~2 hours) (Chen, H. et al., 1999, Cell 98, 675–686.) or treatment of A549 epithelial cells with interleukin-4 (~9 hours) (Shankaranarayanan, P. et al.). Cell-cycle dependent activity of p300/CBP peaks between G1 and S phase, (Ait-Si-Ali, S. et al., 2000, Oncogene 19, 2430–2437.) so FRET change may be observable in arrested populations or single cells. Finally, specific acetylation of K8 near the IFN-β promoter via Gcn5 activation is seen on infection of HeLa cells with Sendai virus (Agalioti, T. et al.).

Once a cellular system is identified in which induced K5 and/or K8 acetylation leads to H4 acetylation reporter FRET increase, we confirm the effect with genetic and pharmacological controls. Mutation studies of the reporter substrate motif are performed to identify the specific lysine positions responsible for FRET change. Also, FRET change should be abolished if the bromodomain is impaired by an N1460A mutation. Third, we immunoprecipitate our reporter from cells and perform Western blot analysis to check that reporter phosphorylation state correlates with FRET response. Fourth, we co-transfect cells with the viral oncoprotein wtE1A, which has been identified as an endogenous inhibitor of p300/CBP (Shankaranarayanan, P. et al.) and should suppress FRET response.

As with the phosphorylation reporter, we also tether the H4 acetylation reporter to H4 itself. The H4-GFP fusion described by Cook et al. (Kimura, H. et al.) does not suffer from misfolding or mis-localization in HeLa cells. We fuse our H4 acetylation reporter to the C-terminal end of the H4 gene and introduce the fusion construct into HeLa cells. The in vivo acetylation responsivity of this targeted reporter is tested as described above for the H3 phosphorylation reporter.

Example 10

Reporters of Protein Methylation

We designed and expressed our first histone methylation reporter based on the HP1 chromodomain. The reporter gave a 20% emission ratio increase on methylation by G9a in vitro. To complete characterization of this reporter, we (1) construct mutant control reporters to check that the FRET response results, as designed, from intramolecular binding of chromodomain to methylated substrate sequence, (2) determine the methylation site(s) responsible for the FRET change (most likely K9), (3) compare methylation kinetics of reporter vs. native H3, and (4) test specificity for methylation mediated by G9a vs. by other enzymes.

Additionally, we determine if the reporter can distinguish between different methylation states of a single lysine side chain. We perform enzymatic mono-, di-, and trimethylation, measure the FRET response, and confirm the methylation state independently using specific methyl-lysine antibodies and mass spectrometry.

Demonstration that the Protein Methylation Reporters Work in the Live Cell Context.

If the in vitro studies show that our HP1-based methylation reporter is specific for H3-K9 methylation, as designed, then we test this reporter inside cells by comparing reporter FRET levels in primary mouse embryonic fibroblasts (PMEFs) and sister cells lacking the H3-K9 methyltransferase SUV39H (Rea, S. et al., 2000, Nature 593–599.). Jenuwein et al. have shown that these SUV39H-null cells display increased levels of phosphorylated H3-S10; since H3-K9 methylation inhibits phosphorylation of the adjacent S10 in in vitro studies, increased S10 phosphorylation is linked to decreased K9 methylation (Rea, S. et al., 2000, Nature 593–599.). Similar observations of reduced K9 methylation, made by Western blot and immunofluorescence staining, have also been made in mouse embryonic stem cells deficient in the histone methyltransferase G9a (Tachibana, M. et al., 2002, Genes Dev. 16, 1779–1791.). We detect methylation level differences in single intact cells using our FRET indicators. Such sister-cell-line comparison assays are also used to road-test reporters for other major lysine methylation sites in H3 (K4, K27).

Example 11

Application of the Reporters to Study the Mechanism of Epigenetic Inheritance of Histone Modification Patterns.

While recent advances have elucidated many of the molecular properties of chromatin, the mechanism by which histone modification patterns are duplicated during cell division remains poorly understood. Except in actively differentiating cells, the histone modification patterns of specific DNA regions are preserved during cell division. For instance, regions of heterochromatin (condensed chromatin which stains intensely with the dye quinacrine and contains large numbers of silenced genes) are enriched in methylated H3 (Lachner, M. et al., 2002, Curr. Opin. Cell Biol. 14, 286–298.) and non-acetylated H4; (Belyaev, N. D. et al., 1996, Exp. Cell Res. 225, 277–285.) these modification patterns are duplicated during cell division to give daughter chromatin with identical domains of heterochromatin. While replication of the DNA sequence itself is mediated by base pairing, and DNA methylation patterns are replicated by DNA methylases which bind hemimethylated DNA, the determinants of H3 methylation and H4 deacetylation specificity are poorly understood.

We use our arsenal of histone modification reporters to investigate the mechanism of specific duplication of histone modification patterns during cell division. Initially, investigate H4 deacetylation during heterochromatin duplication, an area in which some groundwork has already been laid (Taddei, A. et al., 1999, J. Cell Biol. 147, 1153–1166.). We compare the FRET levels of H4 acetylation reporter fused to various scaffolding proteins, and measuring acetylation levels inside single living cells as a function of the cell cycle, to differentiate between several potential models for heterochromatin duplication.

Use of FRET Indicators to Study Histone Modification Pattern Duplication

The indicators we develop are used to study of epigenetic pattern duplication during cell division. Histone modification states are currently detected and analyzed by immunofluorescence staining or chromatin immunoprecipitation (ChIP). In the former, fixed cells are stained by antibodies specific for histone bearing particular modifications. The latter technique involves sequential cell lysis, chromatin isolation based on modification state, and DNA analysis by PCR. Because these methods are both perturbative and involve discontinuous data collection and, for ChIP, averaging over large populations of cells, they tend to compromise spatial and/or temporal resolution. The development of reporters which can dynamically probe the activities of histone-modifying enzymes as a function of chromatin functional environment (high DNA methylation or histone acetylation levels, for example) or cell cycle phase helps clarify the molecular mechanism of epigenetic inheritance.

Our indicators are used to study the heterochromatin duplication process by monitoring the rate and extent of H4 deacetylation as a function of chromatin functional environment (spatial readout) and cell cycle phase (temporal readout). For example, to test the hypothesis that histone deacetylases (HDACs) are specifically targeted to heterochromatin domains through association with heterochromatin-specific proteins, the modification probes are fused to HP1, CAF-1, a methyl-DNA-binding protein (such as the MDB domain of MeCP2), or a chromodomain. If changes in the rate or magnitude of the FRET response in comparison to untargeted probe are observed, roles for the fusion partners in directing HDAC activity during heterochromatin duplication are be implicated. The effect of chromatin functional environment on H4 deacetylation is also probed by looking for patterns of HDAC activity in relation to replication fork clusters. The hypothesis that DNA replication complexes induce the local recruitment and/or activation of HDACs at replication forks predicts that the lowest FRET signals, corresponding to the lowest degree of reporter acetylation, will coincide with replication fork clusters. To visualize replication fork clusters simultaneously in living cells with reporter FRET signals, mRFP- (Campbell, R. E. et al., 2002, *Proc. Natl. Acad. Sci. U.S.A* 99, 7877–7882.) fused HP1 is co-expressed. HP1 is a general marker for heterochromatin, but it is known to concentrate at replication forks clusters (replication forks are visualized as especially bright dots by HP1 immunofluorescence staining) (Taddei, A. et al., 1999, *J. Cell Biol.* 147, 1153–1166.). It should therefore be possible to express low levels of mRFP-HP1 and follow replication fork sites in living cells.

Increases or decreases in reporter FRET as a function of cell cycle phase should also be revealing. If HDAC activity is controlled by DNA replication machinery, reporter FRET must reach a minimum sometime during S phase. If, on the other hand, HDAC activity is constitutively associated with heterochromatin domains, it should be possible to detect deacetylation of the reporter in the vicinity of heterochromatin throughout the entire cell cycle.

Together, these experiments provide a continuous view of dynamic histone modifications in particular chromatin functional environments throughout the cell cycle, helping to differentiate between the various models of heterochromatin duplication.

Equivalents

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety:

I claim:

1. A method of determining the level of histone covalent modification in a biological sample comprising:
   contacting a biological sample with a fusion protein reporter comprising a core comprising a histone-modification-specific binding domain conjugated to a histone polypeptide, wherein the core is flanked by donor and acceptor fluorescent moieties, and
   monitoring the level of fluorescence resonance energy transfer (FRET) between the donor and acceptor fluorescent moieties as a result of contact with the biological sample,
   wherein the level of FRET is a measure of the level of histone covalent modification in the biological sample, and
   wherein the histone covalent modification is acetylation, methylation or phosphorylation.

2. The method of claim 1, wherein the biological sample is selected from the group consisting of cells and tissues.

3. The method of claim 2, wherein the biological sample is a cell.

4. The method of claim 3, wherein the cell is undergoing cell division.

5. The method of claim 1, wherein the histone-modification specific binding domain is conjugated to the histone polypeptide with a linker molecule.

6. The method of claim 1, wherein the fusion protein reporter, further comprises one or more additional histone-modification-specific binding domains.

7. The method of claim 1, wherein the histone polypeptide is selected from the group consisting of H3 and H4.

8. The method of claim 1, wherein the histone polypeptide is selected from the group consisting of the N-terminus of H3 and the N-terminus of H4.

9. The method of claim 1, wherein the donor fluorescent moiety is selected from the group consisting of cyan fluorescent protein (CFP), enhanced cyan fluorescent protein (ECFP), and A206K mutants thereof.

10. The method of claim 1, wherein the acceptor fluorescent moiety is selected from the group consisting of yellow fluorescent protein (YFP), enhanced yellow fluorescence protein (EYFP), Citrine, Venus, and A206K mutants thereof.

11. The method of claim 1, wherein the histone-modification-specific binding domain is selected from the group consisting of 14-3-3, FHA, WW, bromodomain, and chromodomain.

12. The method of claim 11, wherein the bromodomain is selected from the group consisting of Gcn5, $TAF_{11}250$, P/CAF, CBP, BRG1, Swi2, and Sth1.

13. The method of claim 11, wherein the chromodomain is selected from the group consisting of HP1, MRG15, MRG-1, cynCDY, Hrp3, dMi-2, CHD5, Swi6, and pdd3p.

14. The method of claim 1, wherein the histone polypeptide is a polypeptide substrate for the histone-modification-specific binding domain.

15. The method of claim 1, wherein the histone polypeptide is an H3 polypeptide comprising the amino acid sequence set forth as

```
ARTKQTARKSTGGKAPRKQLATKAARKSAP.   (SEQ ID NO:18)
```

16. The method of claim 1, wherein the fusion protein reporter further comprises a targeting polypeptide, associated with the fusion protein.

17. The method of claim 16, wherein the targeting polypeptide is selected from the group consisting of a receptor ligand and a nuclear localization sequence (NLS), nuclear export signal (NES), plasma membrane targeting signal, a histone binding protein, and a nuclear protein.

18. The method of claim 1, further comprising:
monitoring a subsequent second level of FRET in the biological sample, and comparing the first and second levels of FRET as a measure of the change in the level of histone covalent modification in the biological sample.

19. The method of claim 1, further comprising:
comparing the level of fluorescence resonance energy transfer (FRET) in the biological sample to a control level of FRET as a determination of a histone modification disorder in the biological sample.

20. The method of claim 19, wherein the biological sample is from a subject and the determination of a histone modification disorder in the biological sample is diagnostic for a histone modification disorder in the subject.

21. The method of claim 19, wherein the control level of FRET is the level of FRET in a biological sample free of a histone-modification disorder.

22. The method of claim 1, wherein the level of FRET is increased following contact with the biological sample.

23. The method of claim 1, wherein the level of FRET is decreased following contact with the biological sample.

24. A method of determining the level of histone covalent modification in a biological sample comprising
contacting a biological sample with a fusion protein reporter comprising a core comprising a histone-modification-specific binding domain conjugated to a histone polypeptide, wherein the core is flanked by donor and acceptor fluorescent moieties, and
monitoring the level of fluorescence resonance energy transfer (FRET) between the donor and acceptor fluorescent moieties as a result of contact with the biological sample,
wherein the level of FRET is a measure of the level of histone covalent modification in the biological sample, the histone covalent modification is phosphorylation, and the histone-modification-specific binding domain is a 14-3-3, FHA or WW domain.

25. A method of determining the level of histone covalent modification in a biological sample comprising
contacting a biological sample with a fusion protein reporter comprising a core comprising a histone-modification-specific binding domain conjugated to a histone polypeptide, wherein the core is flanked by donor and acceptor fluorescent moieties, and
monitoring the level of fluorescence resonance energy transfer (FRET) between the donor and acceptor fluorescent moieties as a result of contact with the biological sample,
wherein the level of FRET is a measure of the level of histone covalent modification in the biological sample, the histone covalent modification is acetylation, and the histone-modification-specific binding domain is a bromodomain.

26. A method of determining the level of histone covalent modification in a biological sample comprising
contacting a biological sample with a fusion protein reporter comprising a core comprising a histone-modification-specific binding domain conjugated to a histone polypeptide, wherein the core is flanked by donor and acceptor fluorescent moieties, and
monitoring the level of fluorescence resonance energy transfer (FRET) between the donor and acceptor fluorescent moieties as a result of contact with the biological sample,
wherein the level of FRET is a measure of the level of histone covalent modification in the biological sample, the histone covalent modification is methylation, and the histone-modification-specific binding domain is a chromodomain.

* * * * *

UNITED STATES PATENT AND TRADEMARK OFFICE
CERTIFICATE OF CORRECTION

| | | |
|---|---|---|
| PATENT NO. | : 7,056,683 B2 | Page 1 of 1 |
| APPLICATION NO. | : 10/634740 | |
| DATED | : June 6, 2006 | |
| INVENTOR(S) | : Alice Y. Ting | |

It is certified that error appears in the above-identified patent and that said Letters Patent is hereby corrected as shown below:

In the specification, column 1, lines 12-16 the Government Support section should read as follows:

GOVERNMENT SUPPORT

This invention was made with government support awarded by the U.S. Navy under Grant Number N00014-03-1-0456 and by the National Institutes of Health under Grant Number 5-K22-HG002671-02. The government has certain rights in the invention.

Signed and Sealed this

Sixteenth Day of October, 2007

JON W. DUDAS
*Director of the United States Patent and Trademark Office*